(12) United States Patent
Marcu et al.

(10) Patent No.: US 6,803,204 B2
(45) Date of Patent: Oct. 12, 2004

(54) BIOLOGICALLY ACTIVE ALTERNATIVE FORM OF THE IKKα IκB KINASE

(75) Inventors: Kenneth B. Marcu, Stony Brook, NY (US); Margery A. Connelly, Medford, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 152 days.

(21) Appl. No.: 10/188,937

(22) Filed: Jul. 3, 2002

(65) Prior Publication Data

US 2003/0073111 A1 Apr. 17, 2003

Related U.S. Application Data

(62) Division of application No. 09/536,882, filed on Mar. 27, 2000, now Pat. No. 6,489,151.

(51) Int. Cl.$^7$ ................................................ C12Q 1/48
(52) U.S. Cl. ........................................ 435/15; 435/194
(58) Field of Search .................................. 435/15, 194

(56) References Cited

U.S. PATENT DOCUMENTS

| | | |
|---|---|---|
| 5,776,717 A | 7/1998 | Cao |
| 5,804,374 A | 9/1998 | Baltimore et al. |

OTHER PUBLICATIONS

Mock et al., "CHUK, a Conserved Helix–Loop–Helix Ubiquitous Kinase, Maps to Human Chromosome 10 and Mouse Chromosome 19," *Genomics* 27:348–351 (1995).

Margery A. Connelly and Kenneth B. Marcu, "CHUK, a New Member of the Helix–Loop–Helix and Leucine Zipper Families of Interacting Proteins, Contains a Serine–Threonine Kinase Catalytic Domain," *Cellular and Molecular Biology Research* 41: 537–549 (1995).

DiDonato et al., "A Cytokine–Responsive IκB Kinase That Activates The Transcription Factor NF–κB," *Nature* 38817:548–554 (1997).

Regnier et al., "Identification and Characterization of an IκB Kinase," *Cell* 90:373–383 (1997).

Ilana Stancovski and David Baltimore, "NF–κB Activation: The IκB Kinase Revealed?," *Cell Press* 91:299–302 (1997).

McKenzie et al., "Functional Isoforms of IκB Kinase α (Ikkα) Lacking Leucine Zipper and Helix–Loop–Helix Domains Reveal that Ikkα and IKKβ Have Different Activation Requirements," *Molecular and Cellular Biology* 20: 2635–2649(2000).

Woronicz et al., "IκB Kinase–β: NF–κB Activation and Complex Formation with IκB Kinase–α and NIK," *Science* 278:866–869 (1997).

Zandi et al., "The IκB Kinase Complex (IKK) Contains Two Kinase Subunits, IKKα and IKKβ, Necessary for IκB Phosphorylation and NF–κB Activation," *Cell Press* 91: 243–252 (1997).

*Primary Examiner*—Charles L. Patterson, Jr.
(74) *Attorney, Agent, or Firm*—Hoffmann & Baron, LLP

(57) ABSTRACT

The present invention provides isolated IκB kinases that regulate NFκB gene transcription that lack both a leucine zipper like α-helix domain and helix-loop-helix domain. Also provided are the amino acid sequences of these kinases and the nucleotide sequence encoding these kinases, and other related protein and nucleic acid molecules.

5 Claims, 12 Drawing Sheets

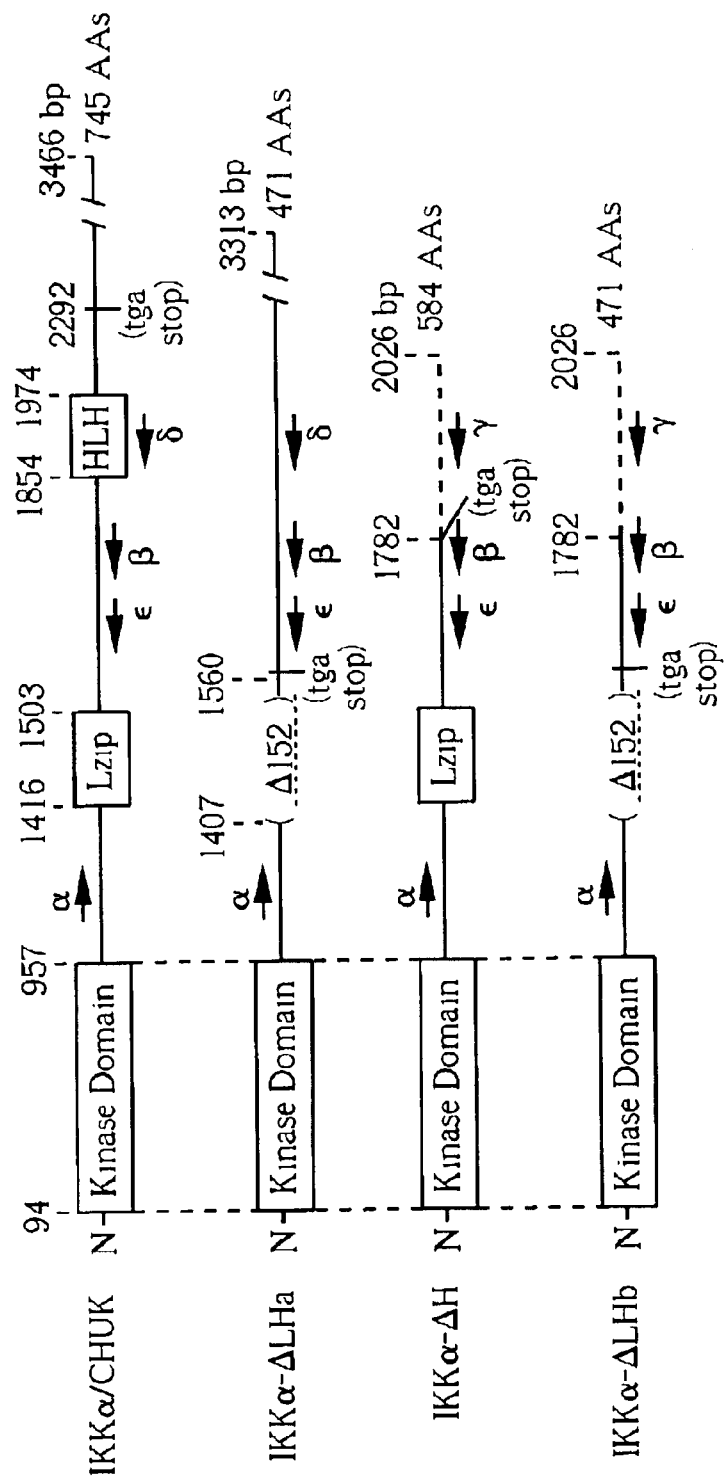
FIG. 1A  FOUR IKKα/CHUK mRNAs

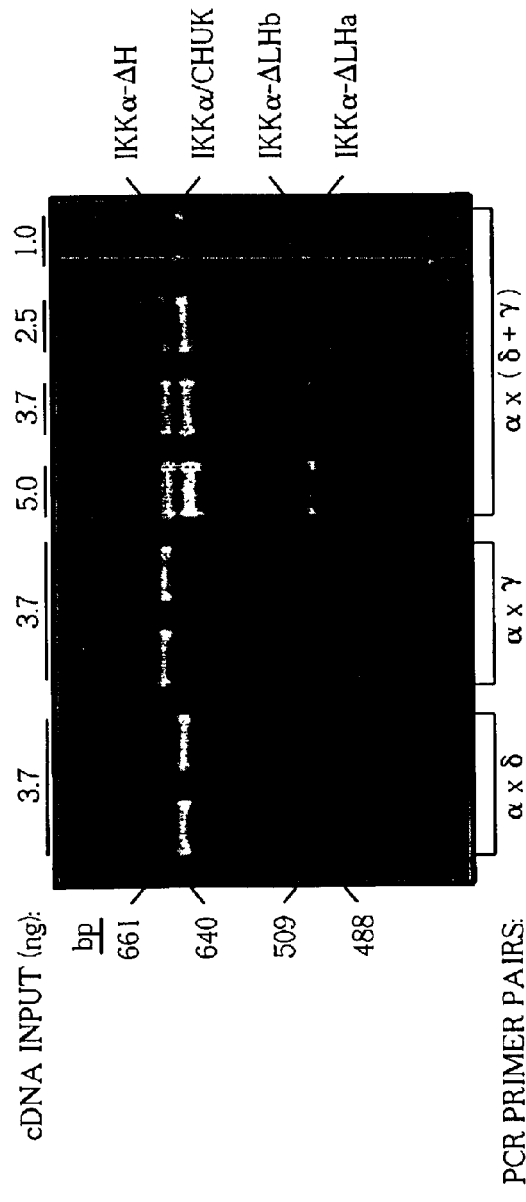
FIG. 1B  RT-PCRS OF MURINE THYMUS RNA

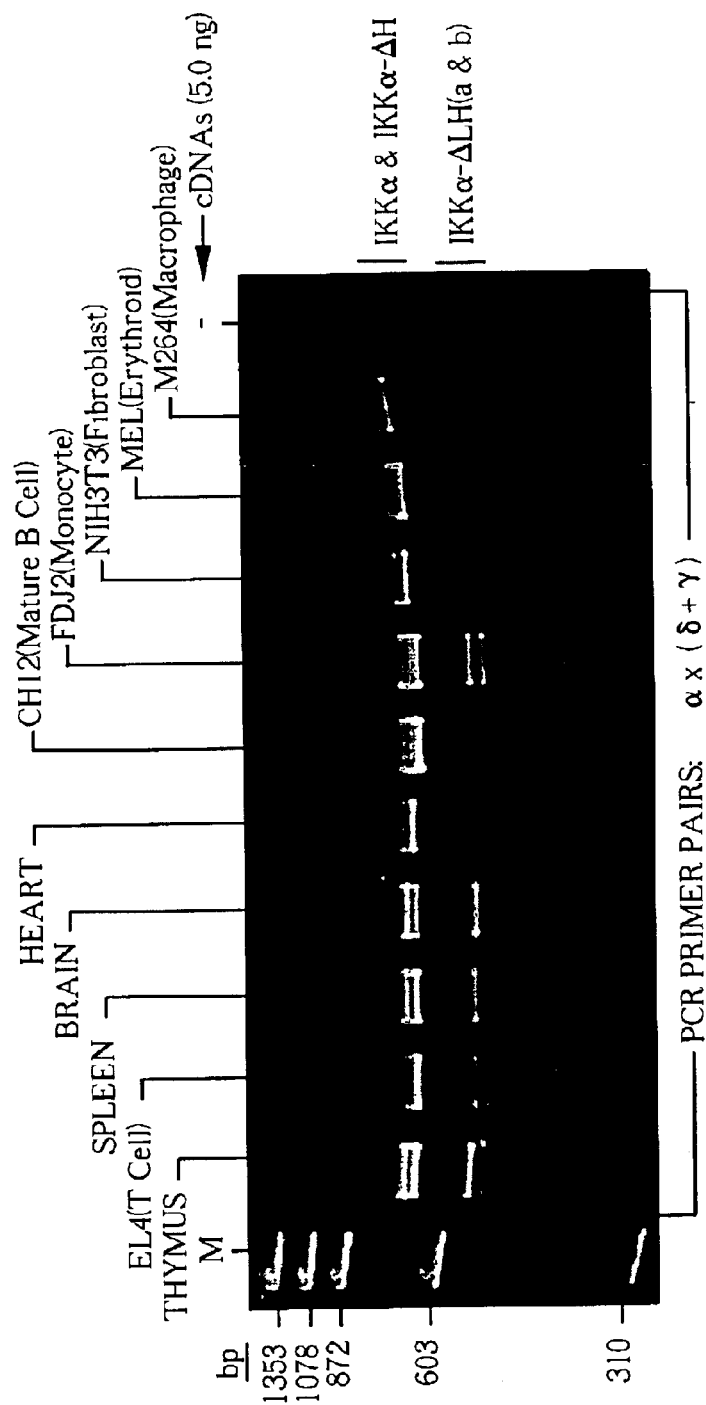
FIG. 2A  IKKα/CHUK ISOFORM EXPRESSION PATTERNS

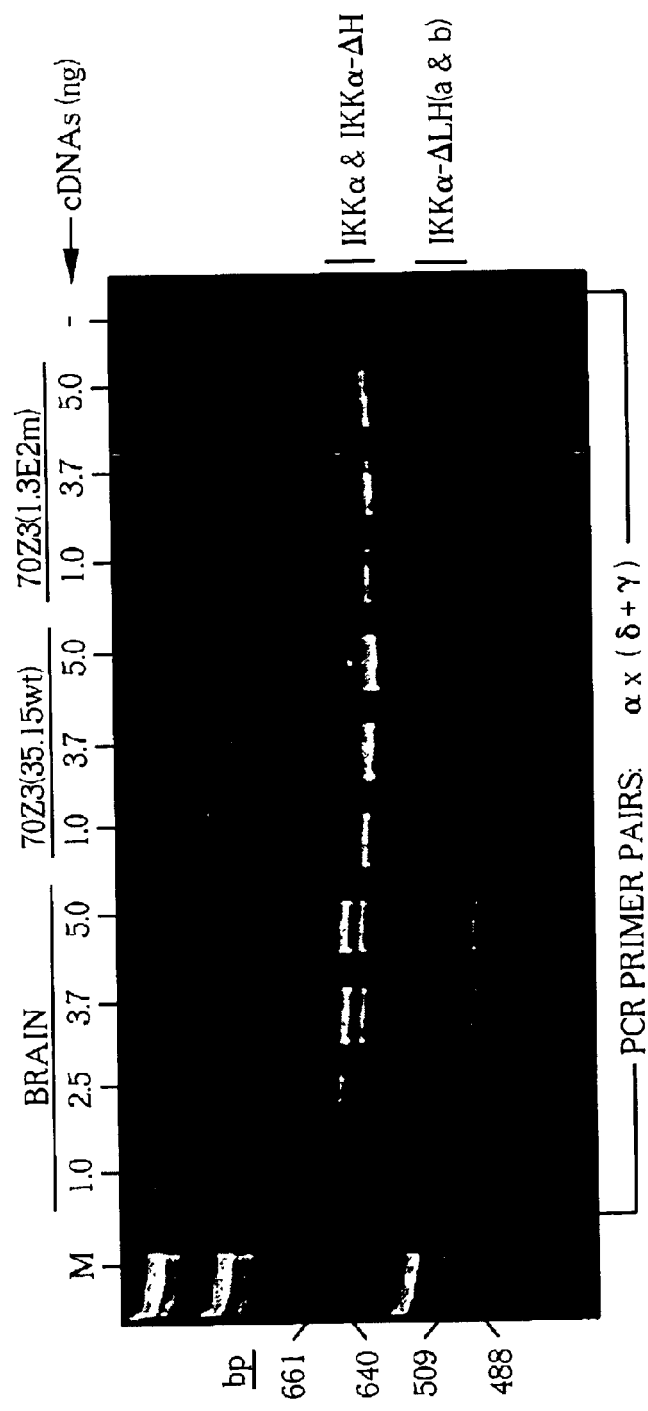
FIG. 2B IKKα/CHUK ISOFORM EXPRESSION PATTERNS

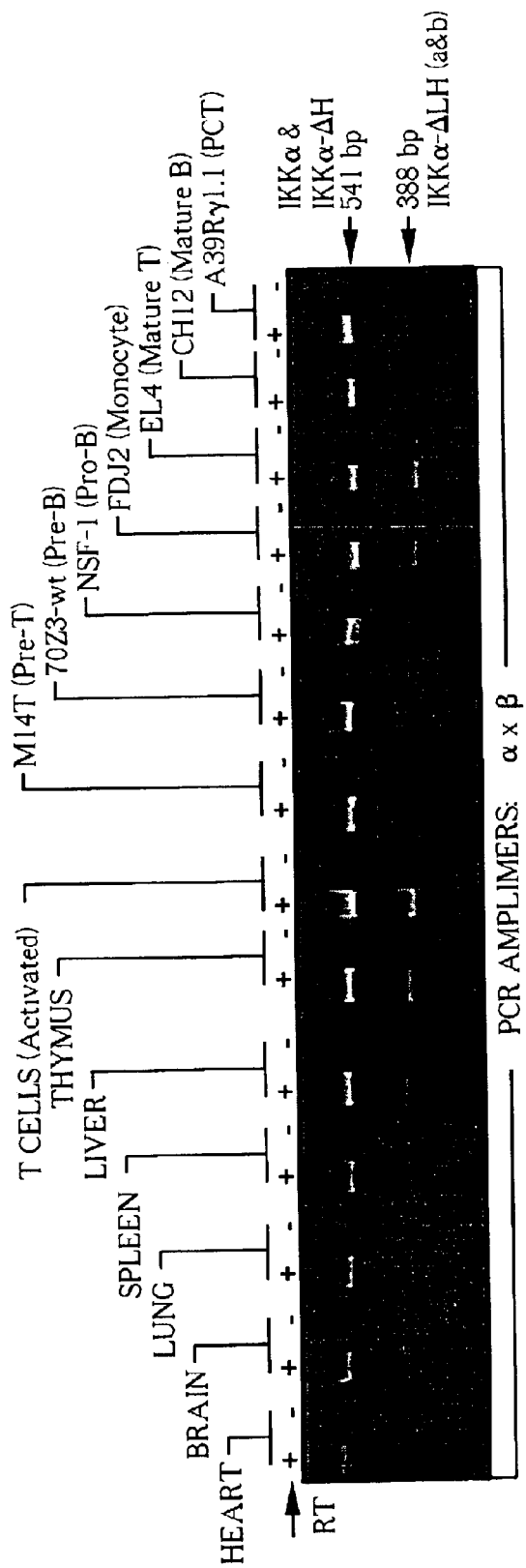
FIG. 3A QUANTITATIVE RT-PCRS OF IKKα/CHUK & IKKα-ΔH VERSUS IKKα-ΔLH

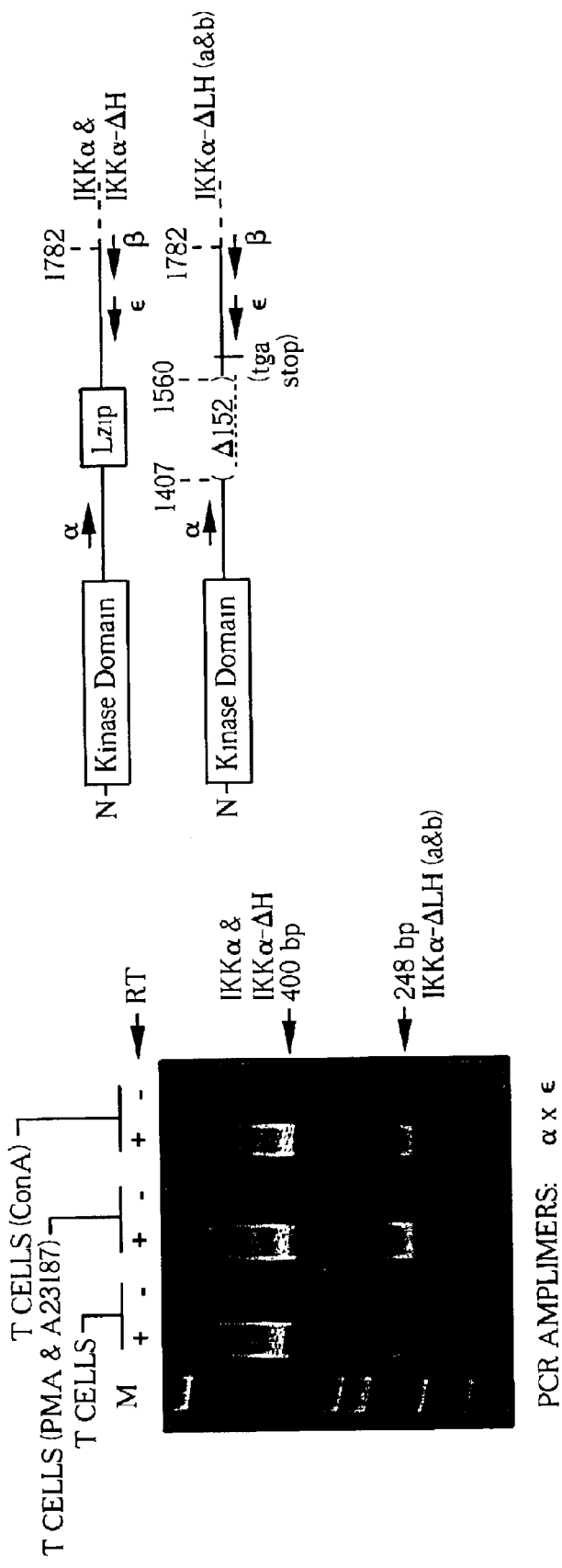
FIG. 3B QUANTITATIVE RT-PCRS OF IKKα/CHUK & IKKα-ΔH VERSUS IKKα-ΔLH

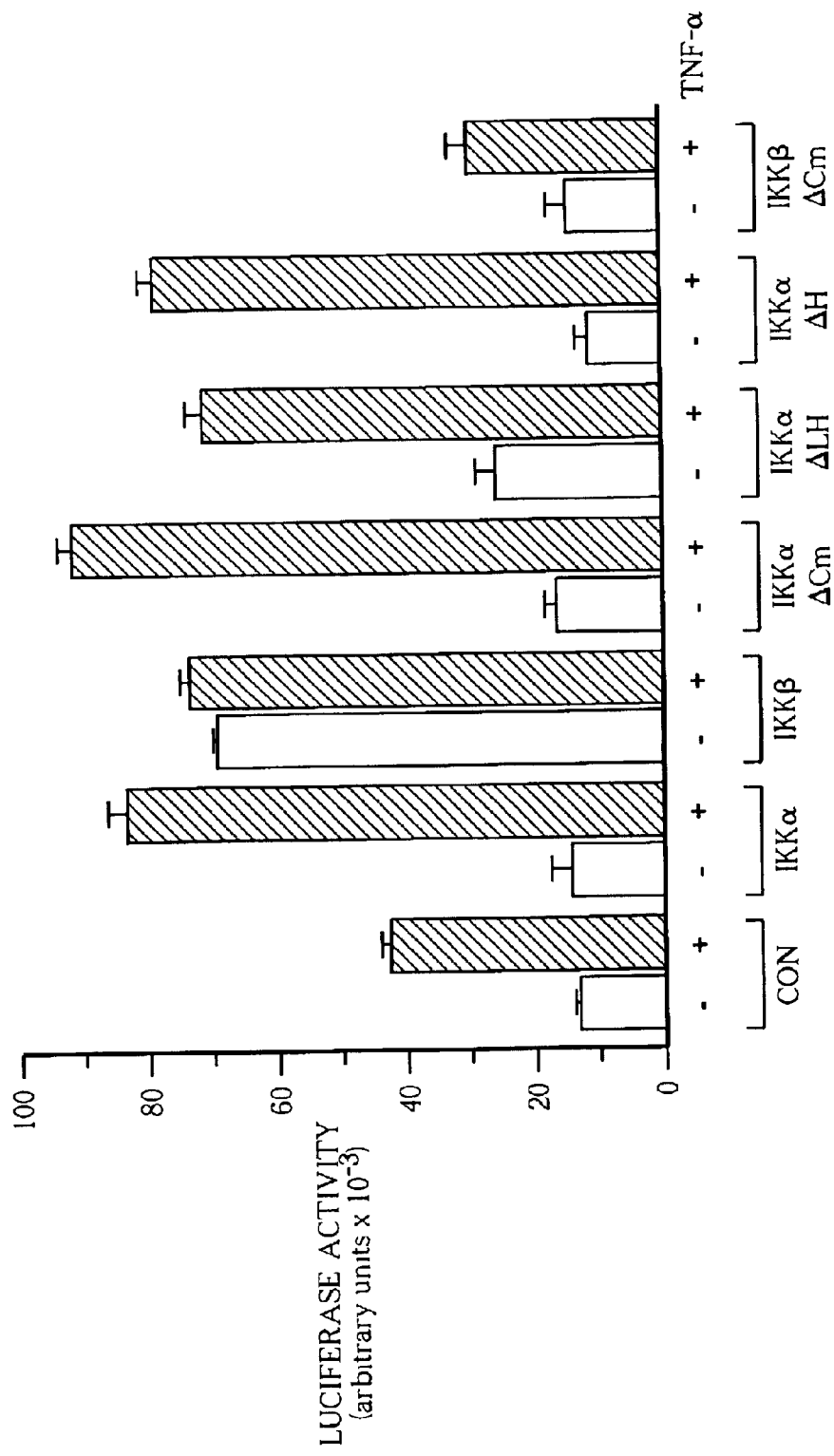
FIG. 4A  IKKα/CHUK ISOFORMS ACTIVATE NF-κB

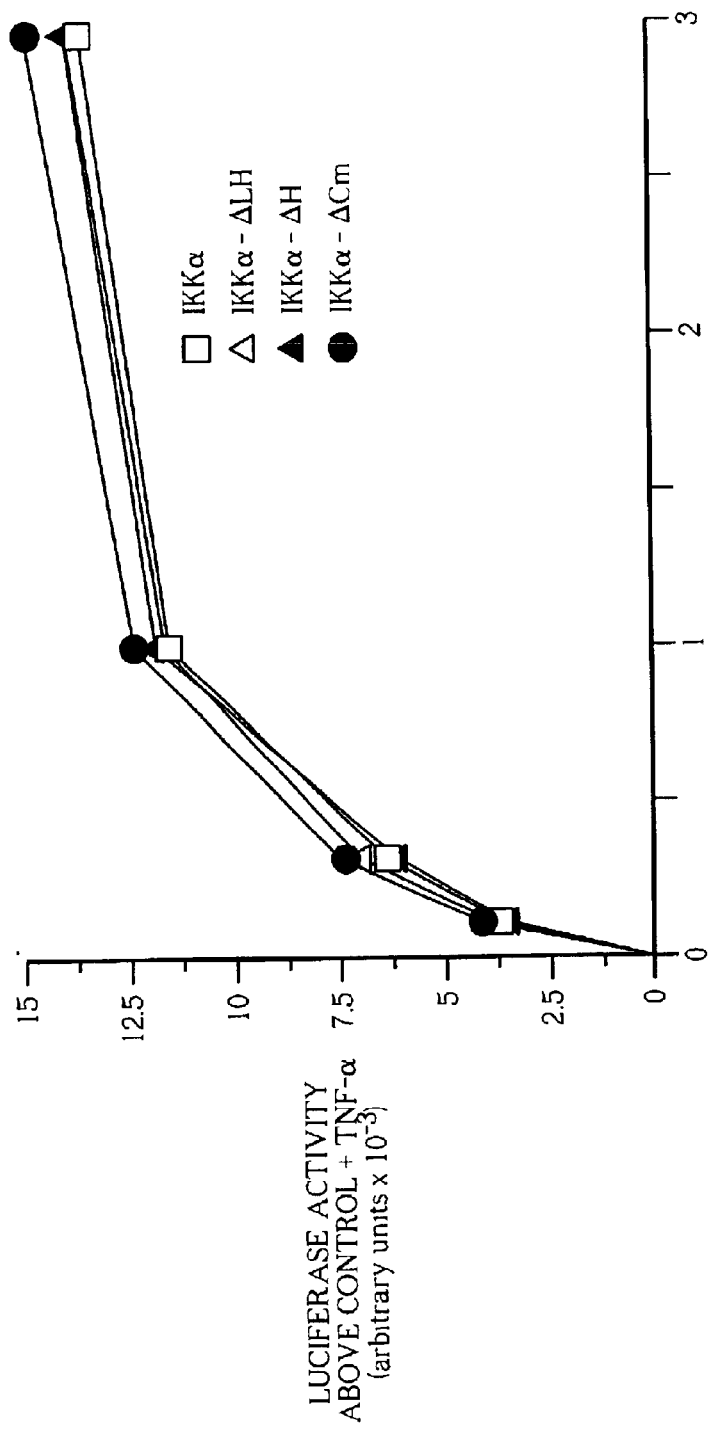
FIG. 4B  IKKα/CHUK ISOFORMS ACTIVATE NF-κB

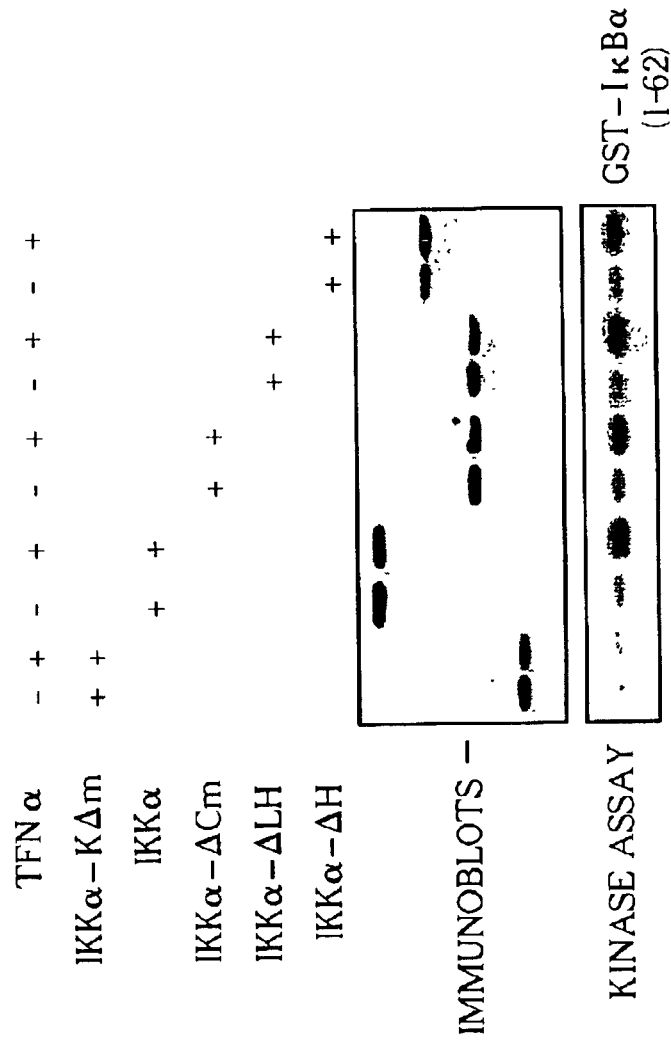
FIG. 5A   IKKα-ΔLH ISOFORMS ARE TNF-α INDUCIBLE IκBα KINASES

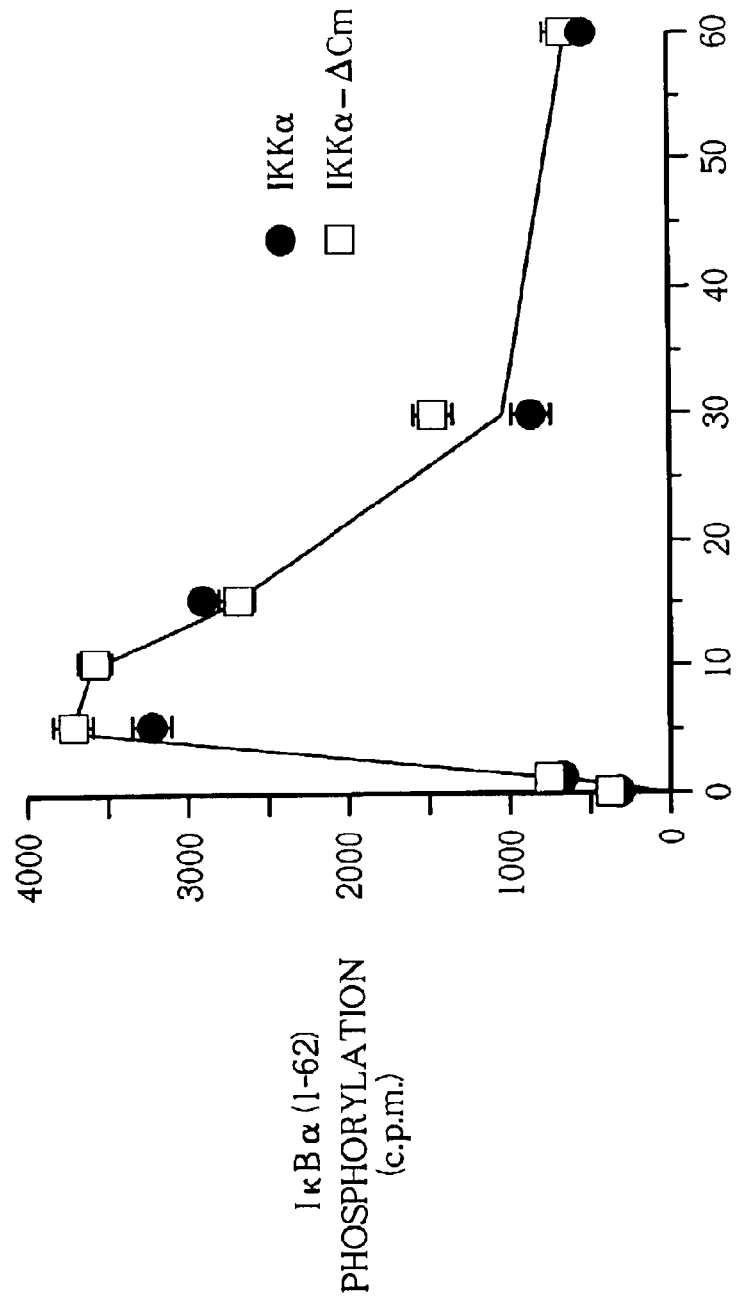
FIG. 5B IKKα-ΔLH ISOFORMS ARE TNF-α INDUCIBLE IκBα KINASES

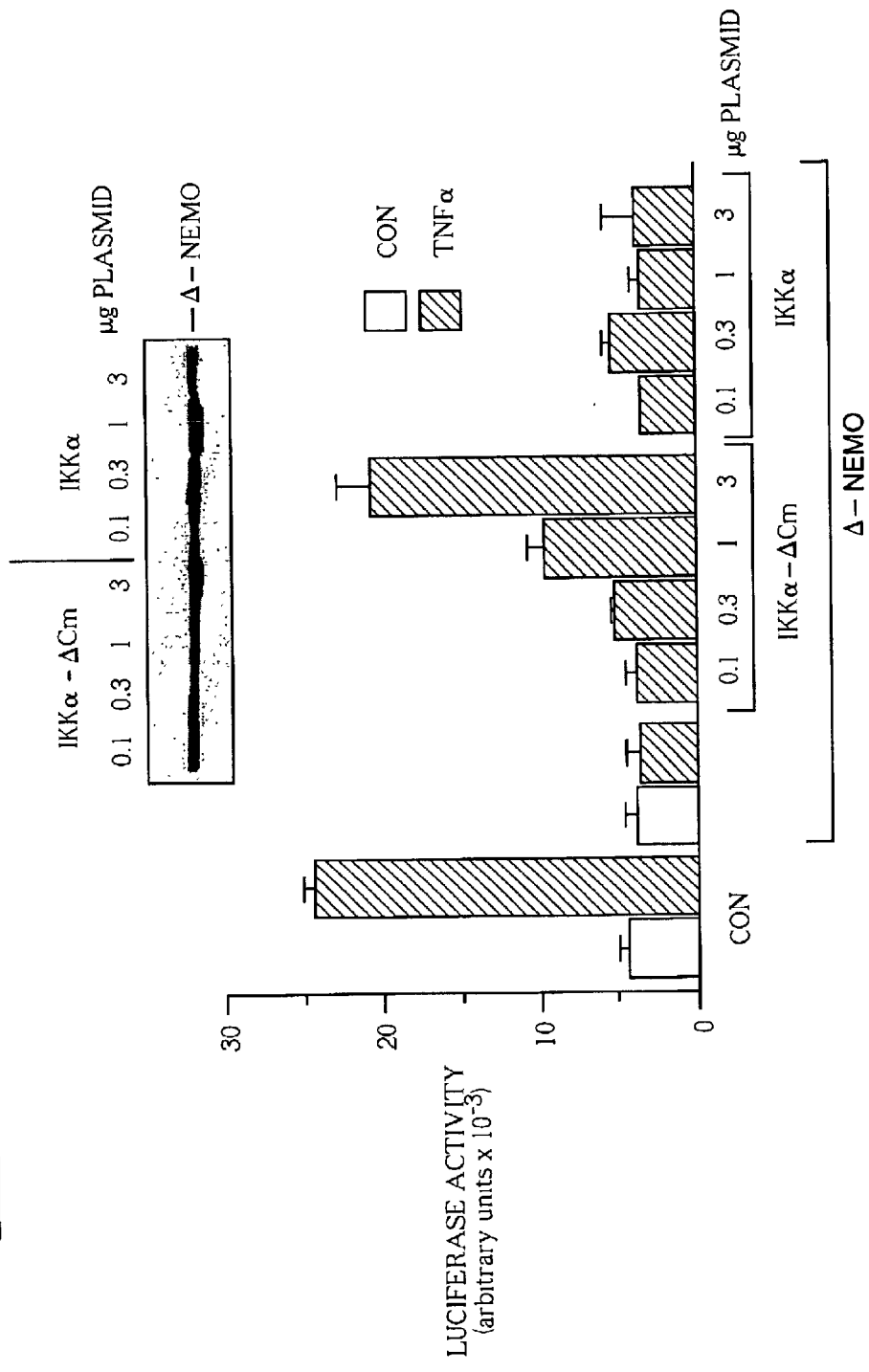
FIG. 7 IKKα-ΔCm RESCUES NF-κB ACTIVATION IN CELLS EXPOSED TO A DOMINANT NEGATIVE NEMO MUTANT BUT IKKα-CHUK CAN NOT

BIOLOGICALLY ACTIVE ALTERNATIVE FORM OF THE IKKα IκB KINASE

CROSS REFERENCE TO RELATED APPLICATIONS

This application is a Divisional Application of U.S. Application Ser. No. 09/536,882, filed on March 27, 2000, now U.S. Pat. No. 6,489,151.

BACKGROUND OF THE INVENTION

The NF-κB family of transcription factors are involved in the regulation of a wide variety of cellular responses. These transcription factors mediate extracellular signals that induce expression of genes which are involved in such diverse processes as cell division, inflammation, and apoptosis. See, for example, Baldwin, Annu. Rev. Immunol. 12, 141–179 (1996); Beg and Baltimore, Science 274, 782–274 (1996); Gilmore et al., Oncogene 13, 1267–1378 (1996); Mayo, et al, Science 278, 1812–1815 (1997); and Van Antwerp et al., Science 274, 787–789 (1996).

NF-κB is anchored in the cytoplasm of most non-stimulated cells by a non-covalent interaction with one of several inhibitory proteins known as IκBs. See for example, Baeuerle and Baltimore, Science 242, 540–546 (1988). Cellular stimuli associated with immune and inflammatory responses, for example inflammatory cytokines such as tumor necrosis factor α (TNFα) or interleukin-1 (IL-1), activate NF-κB by inducing the phosphorylation of IκBs on specific serine residues. Phosphorylation marks the IκBs for ubiquitination and proteosome mediated degradation. The disruption, or dissociation, of IκBs from NF-κB unmasks the NF-κB nuclear localization signal, and facilitates the nuclear translocation of active NF-κB to the nucleus, thereby upregulating NF-κB responsive target genes. See, for example, Baeuerle and Henkel, Annu. Rev. Immunol., 12, 141–179 (1994); Baldwin, Annu.Rev. Immunol., 14, 649–683 (1996); Siebenlist et al., Annu.Rev.Cell Biol. 12, 405–455 (1994); and Verma et al, Genes Dev., 9, 2723–2735 (1995). Thus, this phosphorylation of IκBs is a key regulatory step for NF-κB mediated processes.

Phosphorylation of IκBs on two amino proximal serine residues (for example, in the case of IκBα serines 32 and 36) has long been appreciated to be the major regulatory step in NF-κB activation. See, for example, Baldwin, Annu.Rev. Immunol., 14, 649–683 (1996), Brown et al., Science 267, 1485–1488 (1995); DiDonato et al., Mol. Cell Biol. 16, 1295–1304 (1996); Traenckner et al., EMBO J., 14, 2876–2883 (1995). As such, an important key to elucidating the mechanism of NF-κB activation, and gaining control of the immune and inflammatory responses mediated by NF-κB activation, is determining the kinases involved.

Therefore, there is a need for finding kinases that are involved in the regulation of these processes. Initial attempts to identify the responsible kinase(s) revealed a specific IκB-kinase activity in a large, around 700 kDa, cytoplasmic complex. Chen et al., Genes Dev. 9, 1586–1597 (1995). The activation of this kinase can be mediated by mitogen-activated protein kinase kinase kinase-1 (MEK-1), although the precise mechanism has not yet been established. Lee et al., Cell 88, 213–222 (1997).

Further experiments to decipher the functional connection between TRAFs (TNF-receptor-associated factors) and NF-κB activation led to the isolation of NF-κB-inducing kinase (NIK). Lee et al., Cell 88, 213–222 (1997); and Malinin et al., Nature 385, 540–544 (1997). NIK is a serine/threonine kinase which shares homology to MEKK-1. Phosphorylation of IκB in response to TNFα requires NIK function. Lee et al., Cell 88, 213–222 (1997); and Malinin et al., Nature 385, 540–544 (1997); Song et al. Proc. Natl. Acad. Sci 94, 9792–9796 (1997). However, NIK does not directly phosphorylate NF-κB. Lee et al., Cell 88, 213–222 (1997).

Of critical importance for elucidating, and controlling, the signaling pathways that lead to NF-κB activation is the determination and characterization of kinases that directly phosphorylate IκB. The abbreviation "IKK" is used to designate an IκB kinase. Recently, an IκB kinase (IKK), designated IKKα, was identified in a yeast-two-hybrid screen with NIK as bait. Regnier et al., Cell 90, 373–383 (1997). IKKα was also purified using conventional biochemical techniques and determined to be the major IκB kinase activity induced by TNF stimulation of HeLa cells. DiDonato et al., Nature 388, 548–554 (1997). IKKα had been cloned previously in a reverse transcriptase polymerase chain reaction (RT-PCR) based search for myc-like genes containing helix-loop-helix domains and was termed CHUK (conserved helix-loop-helix ubiquitous kinase). Connelly and Marcu, Cellular and Molecular Biology Research 41, 537–549 (1995). CHUK was renamed IKKα when its function was discovered. Regnier et al. (1997). The identification of IKKα (CHUK) as a cytoplasmic kinase which phosphorylates IκB family members at their physiologically relevant sites and targets them for proteosome-mediated degradation was a major breakthrough.

The IKKα (CHUK) gene encodes a 745 amino-acid polypeptide (having a molecular mass of approximately 85 kDa). Murine and human IKKα (CHUK) cDNA clones were found to be almost identical. Connelly and Marcu, Cellular and Molecular Biology Research 41, 537–549 (1995). Another kinase, termed IKKβ, homologous to IKKα, has also been reported. Stancovski and Baltimore, Cell 91, 299–302 (1997); Woronicz et al., Science 278, 866–869 (1997); and Zandi et al. Cell 91, 243–252 (1997). IKKα and IKKβ have 52% overall similarity to each other and 65% identity in the kinase domain. Zandi et al., Cell 91, 243–252 (1997). IKKα and IKKβ share two carboxy-proximal structural domains, leucine zipper and H-L-H. (Connelly and Marcu, 1995). Since these domains are thought to play roles in protein—protein interactions, the IKKs may employ these domains to recruit proteins involved in their regulation or to facilitate binding to specific substrates. Recent experiments on the regulation of IKKβ activation suggest that the probable interaction of the carboxy-proximal H-L-H and amino-proximal catalytic domains are required for its cytokine induced activation. (Delhase et al., 1999). An IκB kinase termed T2K has been described in U.S. Pat. No. 5,776,717 to Cao.

The known IκB protein kinases generally phosphorylate IκBs at specific serine residues. For example, they specifically phosphorylate serines 32 and 36 of IκBα. Phosphorylation of both sites is required to efficiently target IκBα for destruction in vivo. Moreover, activation of IKKα and IKKβ occurs in response to NF-κB activating agents and mutant IKKα and IKKβ that are catalytically inactive block NF-κB stimulation by cytokines. These results highlight the important role played by IκB protein kinases in NF-κB activation processes. See Stancovski and Baltimore, Cell 91, 299–302 (1997) for a recent discussion of IκB kinases.

IKKα (CHUK) and IKKβ have structural motifs characteristic of the IKKs. This includes an amino terminal serine-threonine kinase domain separated from a carboxyl proximal helix-loop-helix (H-L-H) domain by a leucine zipper-like amphipathic α-helix structure. These structural characteristics are unlike other kinases and the domains are thought to be involved in protein—protein interactions. The IKKs may employ these domains to recruit proteins involved in their regulation or to facilitate binding to specific substrates. Recent experiments on the regulation of IKKβ activation suggest that the probable interaction of the H-L-H and the kinase domains are required for its cytokine-induced activation (Delhase et al., 1999).

The discovery of IKKs will facilitate elucidation of the events triggered by the engagement of cytokine receptors which lead to the activation of the cytoplasmically anchored NF-κB transcription factors. This is of great importance because NF-κB gene regulation is involved in a host of pathological events, in addition to inflammatory processes. For example, NF-κB gene regulation has been implicated in the progression of acquired immune deficiency syndrome (AIDS), acute phase response, activation of immune and endothelial cells during toxic shock, allograft rejection, and radiation responses. Knowledge of the mechanisms of NF-κB activation will be invaluable in the development of therapeutic agents for these conditions.

Significantly, the discovery of kinases that are involved in activating NF-κB by phosphorylating IκBs is critical for developing means for controlling cellular processes regulated by NF-κB. In particular, there is a need for inhibitors of IκB phosphorylation that can be used to control undesirable inflammation and immune responses. Protein kinases that act at the key regulatory step of NF-κB activation provide targets for the development of inhibitors of such responses. Discovery of additional kinases involved in the phosphorylation of IκBs would aid in the rational development of means for controlling cellular processes regulated by the NF-κB system. Thus, there is a need for the identification and characterizing of kinases that phosphorylate IκB.

An IκB protein kinase which has a kinase domain, a leucine zipper like α-helix domain and no helix-loop-helix has been identified (IKKα-ΔH) (U.S. Ser. No. 09/160,483). IKKα-ΔH is useful as a target for the development of inhibitors of IκB phosphorylation and anti-inflammatory therapeutics.

However, a better target would be an IκB protein kinase which further lacks the leucine zipper like α-helix domain. Drugs that inhibit such a target would be specifically directed to the protein's kinase catalytic domain without other interacting factors thereby providing a higher specificity of action.

The object of the present invention is to discover new IKK molecules.

SUMMARY OF THE INVENTION

These and other objects, as will be apparent to those having ordinary skill in the art, have been met by providing an isolated IκB protein kinase that has a kinase domain and has neither a leucine zipper like α-helix domain nor a helix-loop-helix domain (IKKα-ΔCm). A preferred embodiment of the invention is an isolated protein having the amino acid sequence set forth in SEQ ID NO:1. Also included in this invention is an isolated IκB protein kinase that contains a unique twenty amino acid sequence at the carboxy-terminal end of IKKα-ΔCm, designated as IKKα-ΔLH, and has the amino acid sequence set forth in SEQ ID NO:4. Also included in this invention are isolated nucleic acid molecules that encode the IκB protein kinase that have a kinase domain and have neither a leucine zipper like α-helix domain nor a helix-loop-helix domain. (SEQ ID NO:2, SEQ ID NO:5 and SEQ ID NO:6). Methods of making IKKα-ΔLH and IKKα-ΔCm by expressing nucleic acid molecules encoding the protein are also provided. Antibodies directed to IKKα-ΔLH and IKKα-ΔCm are also included in the invention.

The invention also includes a method of screening for an agent which modulates IκB phosphorylation by the IκB kinase that has a kinase domain and has neither a leucine zipper like α-helix domain nor a helix-loop-helix domain, the method comprising the steps of:

incubating a mixture comprising:
the IκB kinase, and
a candidate modulating agent;
detecting an agent-biased phosphorylation level of the IκB kinase in the presence of the, a candidate modulating agent;
detecting an agent-independent phosphorylation level of the IκB kinase in the absence of the candidate modulating agent;
comparing the agent-biased phosphorylation level with the agent-independent phosphorylation level;
selecting the candidate modulating agent that exhibits a significant difference between the agent-biased phosphorylation level and the agent-independent phosphorylation level.

DESCRIPTION OF THE FIGURES

FIG. 1A is a schematic representation that compares the domain structures of murine IKKα, murine IKKα-ΔLHa, murine IKKα-ΔH, and murine IKKα-ΔLHb.

FIG. 1B is RT-PCR analysis of IKKα isoform expression patterns of Murine Thymus RNA.

FIG. 2A is RT-PCR analysis of IKKα isoform expression patterns of Murine Tissues.

FIG. 2B is RT-PCR analysis of IKKα isoform expression patterns of Murine Brain.

FIGS. 3A and B are quantitative RT-PCR analyses of IKKα isoform expression patterns of Murine Tissues and established cell lines.

FIG. 4A is a bar graph showing the relative abilities of IKKα isoforms to activate the NF-κB reporter gene.

FIG. 4B is expression plasmid dose response curves of IKKα isoforms.

FIG. 5A are Immunoblots and Kinase Assays of IKKα isoforms.

FIG. 5B is a graph of the time course of Phosphorylation of IKKα isoforms.

FIG. 7 is a bar graph showing the NF-κB activation in IKKα isoforms exposed to a dominant negative NEMO mutant.

DETAILED DESCRIPTION OF THE INVENTION

Figure 6:
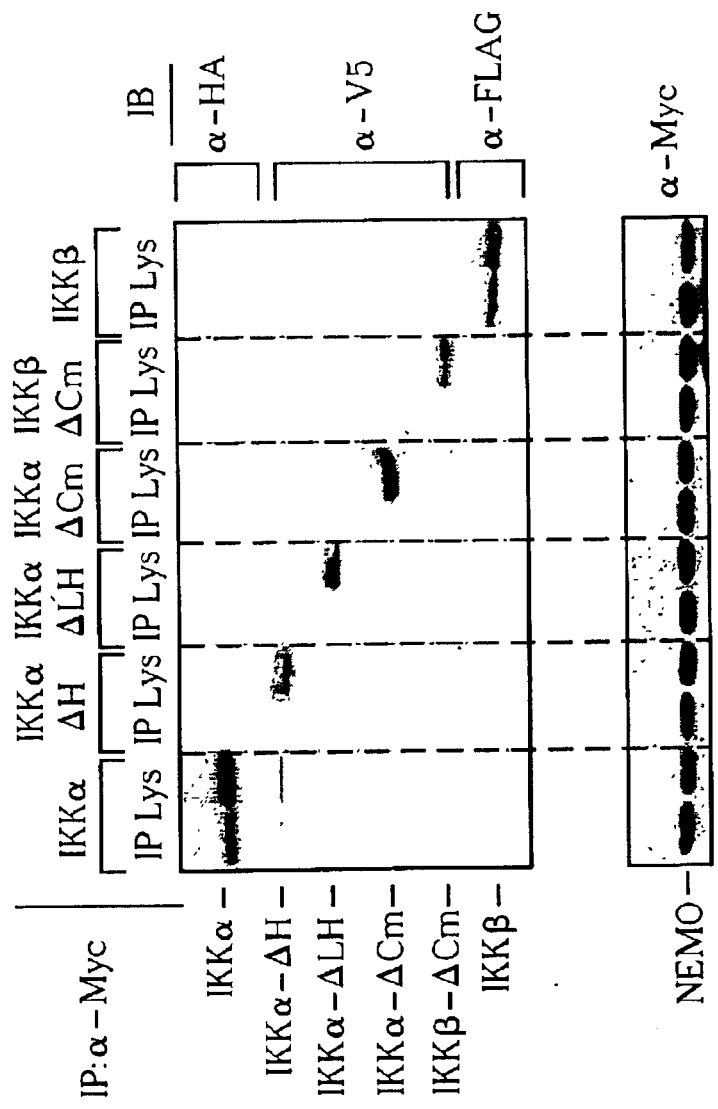
FIG. 6 are immunoblots of co-immunoprecipitations of IKKα, IKkα-ΔH, IKKα-ΔLH, IKKα-ΔCm, IKKβ/CHUK and NEMO/IKKα co-transfectd into HEK293 cells to determine which IKK isoforms have the capacity to interact with NEMO in vivo.

The invention is directed to IκB protein kinases which lack the leucine zipper and helix-loop-helix domains of IKKα. Protein kinases are enzymes that phosphorylate proteins at defined locations. The sites of phosphorylation are usually the hydroxyl groups of Ser and Thr amino acid residues, although Tyr, His, and Lys can also be phosphorylated depending on the kinase and the structure of the substrate protein. The leucine zipper domain (LZ) and the helix-loop-helix domain (H-L-H) were hitherto known as common structural motifs found in proteins that bind DNA.

In one embodiment, the invention provides an isolated IκB protein kinase (IKKα-ΔCm) which has a kinase domain and, has neither a helix-loop-helix domain nor a leucine zipper like α-helix domain. The kinase domain can be a Serine/Threonine kinase domain. A preferred embodiment of the invention is an isolated protein having the amino acid sequence set forth in SEQ ID NO: 1. IKKα-ΔCm can be a recombinant mutant.

Also included in this invention is an isolated IκB protein kinase that contains a unique twenty amino acid sequence at the carboxy-terminal end of IKKα-ΔCm. This protein kinase is designated as IKKα-ΔLH, and has the amino acid sequence set forth in SEQ ID NO:4. The unique twenty amino acid sequence is set forth in SEQ ID NO:3 (IFRKNVKSMERNGRKGHSLF). As long as IκB kinase function is maintained, IKKα-ΔLH can have a kinase domain and either the unique twenty amino acid carboxyl terminal domain or additional amino acids at the carboxyl terminal end. The kinase domain can be a Serine/Threonine kinase domain.

IKKα-ΔLH is a previously unknown cellular isoform of IKKα. IKKα-ΔLH shares a similar primary structure to IKKα from the N-terminal region through amino acid 451 (prior to the leucine zipper region of IKKα) whereupon IKKα-ΔLH diverges. IKKα-ΔLH is a polypeptide of about 50 kDa, specified by 471 amino acids. The kinase domain of this polypeptide includes a region from about amino acid 15 to about amino acid 301.

Akin to IKKα/CHUK, the IKKα-ΔLH and IKKα-ΔCm proteins are TNF-α inducible, NF-κB activating IκBα kinases. By a combination of NF-κB element driven luciferase gene reporter assays, immune complex kinase assays and co-immunoprecipitations with other known components of the approximately 700–900 kD IKK complex, the IKKα-ΔLH and IKKα-ΔCm proteins were found to behave in a similar fashion to full length IKKα/CHUK by several criteria. First, expression plasmid dose response curves reveal that each form of IKKα/CHUK activates a comparable level of NF-κB luciferase activity even at their limiting dosages (FIG. 4B). Second, each form of IKKα/CHUK correctly phosphorylates IκBα (on serines 32 and 36) in response to TNFα signaling (FIG. 5A). Third, IKKα-ΔCm activates NF-κB and phosphorylates IκBα with an enzymatic time course superimposable with full length IKKα/CHUK. (FIG. 5B.) Fourth, like IKKα/CHUK, IKKα-ΔCm's ability to activate NF-κB is not appreciably enhanced by co-expression with IKKβ and is inhibited by a kinase inactive, ATP binding domain mutant of IKKα/CHUK. Therefore, these isoforms of IKKα/CHUK, which lack the LZ and H-L-H domains, retain a number of functions of the full length IKKα/CHUK. It is surprising that the carboxy-tail domain of the full length IKKα/CHUK does not significantly contribute to the kinase's functional activity.

The H-L-H and LZ domains are thought to play roles in protein—protein interactions. It is believed that the H-L-H domain plays a critical role in the proper structural orientation of the protein required for functionality. The LZ domain has been found to be required for heterodimerization of IKKα with IKKβ. It is thought that this LZ-linked heterodimer interfaces with other upstream activating kinases like NIK, MEKKI and AKT presumably via the actions of adaptor or docking factors like NEMO and IKAP. The IKKα/IKKβ heterodimer is believed to be crucial for IκB phosphorylation. Therefore, it was unexpected that IKKα-ΔLH and IKKα-ΔCm are cytokine-inducible IκB kinases although they do not associate with either IKKα or IKKβ. Even more surprising is that IKKα-ΔLH and IKKα-ΔCm are more potent at upregulating NF-κB in response to cytokine stimulation than known IκB kinases such as IKKα.

Thus, IKKα-ΔLH and IKKα-ΔCm are functional IκB kinases that respond to inflammatory cytokines as monomeric proteins. Because of their novel structure and capacity to act as monomers, IKKα-ΔLH and IKKα-ΔCm provide a unique target for the development of inhibitors of IκB phosphorylation and for obtaining anti-inflammatory therapeutics. Drugs which inhibit IKKα-ΔLH and IKKα-ΔCm could be specifically directed to the protein's kinase catalytic domain without other interacting factors thereby providing a much higher specificity of action.

In surprising contrast to the full length IKKα/CHUK transcript, RT-PCR analysis reveals that IKKα-ΔLHa and b are differentially expressed in normal murine tissues and established cell lines (FIGS. 2 and 3). IKKα/CHUK is the predominant mRNA in most instances except for thymus and brain. In normal T lymphocytes, transcripts encoding the smaller IKKα/CHUK polypeptides predominate over full length IKKα/CHUK and the relative steady state amounts of the IKKα-ΔLH isoforms are also preferentially increased by T cell mitogenic stimuli. Preferential expression of the IKKα-ΔLH isoforms are also observed for the EL4 mature T cell lymphoma while they are very weakly expressed in immature T, immature and mature B cells and most other cell types (FIGS. 2A, 2B & 3A).

The invention further includes minor modifications, and all naturally occurring alleles, of the polypeptide set forth in SEQ ID NO:1 or SEQ ID NO:4 that result in proteins which have substantially equivalent activity. Modifications may be deliberate, as by site-directed mutagenesis, or may be spontaneous mutations. Alleles may be from any species. The invention includes all of these polypeptides so long as IKKα-ΔCm or IKKα-ΔLH activity is retained.

For example, the invention also includes conservative variations or equivalent variants of SEQ ID NO:1 or SEQ ID NO:4. The terms "conservative variation" and "equivalent variant" as used herein denote the replacement of amino acids by other amino acids that have similar chemical and biological properties, or that are generally considered equivalent.

For example, it is known in the art to substitute amino acids in a sequence with equivalent amino acids, i.e. conservative variations. Groups of amino acids normally considered to be equivalent are:

(a) Ala (A), Ser (S), Thr (T), Pro (P), Gly (G);
(b) Asn (N), Asp (D), Glu (E), Gln (Q);
(c) His (H), Arg (R), Lys (K);
(d) Met (M), Leu (L), Ile (I), Val (V); and
(e) Phe (F), Tyr (Y), Trp (W).

Substitutions, additions, and/or deletions in the protein sequences may be made as long as the function of the proteins of the invention is maintained. Equivalent proteins will normally have substantially the same amino acid sequence as the native proteins. An amino acid sequence that is substantially the same as another sequence, but that differs from the other sequence by means of one or more substitutions, additions and/or deletions, is considered to be an equivalent sequence, equivalent variant or conservative variation. Preferably, less than 25%, more preferably less than 10%, of the number of amino acid residues in a sequence are substituted for, added to, or deleted from the proteins of the invention.

The proteins of the invention are isolated. The term "isolated" as used herein, in the context of proteins, refers to an IKKα-ΔLH polypeptide which is unaccompanied by at least some of the material with which it is associated in its natural state. The isolated protein constitutes at least 0.5%, preferably at least 5%, more preferably at least 25% and still more preferably at least 50% by weight of the total protein in a given sample. Most preferably the "isolated" protein is substantially free of other proteins, lipids, carbohydrates or other materials with which it is naturally associated, and yields a single major band on a non-reducing polyacrylamide gel.

The invention also provides isolated nucleic acid molecules that encode IKKα-ΔLH or IKKα-ΔCm and the variants of these proteins described herein.

An isolated nucleic acid molecule that encodes IKKα-ΔCm is set forth in SEQ ID NO:2. Isolated nucleic acid molecules, designated as IKKα-ΔLHa and IKKα-ΔLHb, both encode IKKα-ΔLH and are set forth in SEQ ID NO:5 and 6 respectively. A comparison of the domain structures of murine IKKα, murine IKKα-ΔLHa, and murine IKKα-ΔLHb is shown in FIG. 1A. IKKα-ΔLHa and IKKα-ΔLHb, possess the identical 152 bp deletion of IKKα/CHUK (nucleotides 1408–1559) [numbered according to (Connelly and Marcu, 1995)]. This internal 152 bp deletion removes the leucine zipper domain downstream of residue 451. The same deletion changes the remainder of the translation reading frame to encounter a termination codon after a short stretch of twenty unique amino acids. The IKKα-ΔLHa transcript is otherwise identical to the full length IKKα/CHUK mRNA. The IKKα-ΔLHb isoform contains the same 3' noncoding sequence as IKKα-ΔH, inserted after IKKα/CHUK nucleotide 1782.

Nucleic acid molecules (nucleic acids) of the invention include deoxyribonucleic acid (DNA), complementary DNA (cDNA), and ribonucleic acid (RNA) sequences that encode an IKKα-ΔCm or IKKCα-ΔLH protein, or a unique fragment thereof. Such nucleic acids include naturally occurring, synthetic, and intentionally manipulated nucleic acid molecules. For example, the polynucleotide sequence may be subjected to site-directed mutagenesis.

Fragments include primers and probes which are useful as tools in molecular biology and biotechnology. For example, the fragment can be used as a primer ("amplimer") to selectively amplify nucleic acid, such as genomic DNA or total RNA. Primers can also be used in nucleic acid amplification procedures such as the polymerase chain reaction (PCR), ligase chain reaction (LCR), Repair Chain Reaction (RCR), PCR oligonucleotide ligation assay (PCR-OLA), and the like.

The fragment can also be an oligonucleotide complementary to a target nucleic acid molecule, i.e., the fragment can be a probe. Such oligonucleotides can be DNA or RNA. Oligonucleotides useful as probes in hybridization studies, such as in situ hybridization, can also be constructed.

The length of the oligonucleotide probe is not critical, as long as it is capable of hybridizing to the target molecule. The oligonucleotide should contain at least 6 nucleotides, preferably at least 10 nucleotides, and more preferably, at least 15 nucleotides. There is no upper limit to the length of the oligonucleotide probes. Longer probes are more difficult to prepare and require longer hybridization times. Therefore, the probe should not be longer than necessary. Normally, the oligonucleotide probe will not contain more than 50 nucleotides, preferably not more than 40 nucleotides, and, more preferably, not more than 30 nucleotides.

Numerous methods for detectably labeling such probes with radioisotopes, fluorescent tags, enzymes, binding moieties (e.g., biotin), and the like are known, so that the probes of the invention can be adapted for easy detectability. Methods for making and using nucleic acid probes are understood by those skilled in the art. See, for example, Keller G H and Manak M M, *DNA Probes,* 2d ed., Macmillan Publishers Ltd., England (1991) and Hames B D and Higgins S J, eds., *Gene Probes I and Gene Probes II*, IRL Press, Oxford (1995).

Antisense nucleic acid sequences and nucleic acid sequences that are degenerate as a result of the genetic code are also within the scope of the invention. There are 20 natural amino acids, most of which are specified by more than one codon. Therefore, all degenerate nucleotide sequences are included in the invention as long as the amino acid sequence of the IKKα-ΔCm or IKKαΔHL polypeptide encoded by the sequence is functional, i.e. phosphorylates IκB. Thus, the invention also includes all nucleic acid molecules that encode a polypeptide having an amino acid sequence as set forth in SEQ ID NO: 1 or SEQ ID NO:4.

The nucleic acid molecules are of synthetic (non-natural) sequences and/or they are isolated. The term "isolated" as used herein, in the context of nucleic acids, includes nucleic acid molecules unaccompanied by at least some of the material with which they are associated in their natural state. The isolated nucleic acid constitutes at least 0.5%, preferably at least 5%, more preferably at least 25% and still more preferably at least 50% by weight of the total nucleic acid in a given sample. Most preferably the "isolated" nucleic acid is substantially free of other nucleic acids, proteins, lipids, carbohydrates or other materials with which it is naturally associated. The nucleic acid molecules of the invention can also be recombinant, meaning that they comprise a non-natural sequence or a natural sequence joined to nucleotide(s) other than than those in which they are joined on the natural chromosome.

Proteins and nucleic acid molecules homologous and substantially homologous to SEQ ID NO: 1, SEQ ID NO:4 and SEQ ID NO:2, SEQ ID NO:5, SEQ ID NO:6, respectively, are also included in the invention.

In the present specification, the sequence of a first nucleotide sequence is considered homologous to that of a second nucleotide sequence if the first sequence is at least about 30% identical, preferably at least about 50% identical, and more preferably at least about 65% identical to the second nucleotide sequence. In the case of nucleotide sequences having high homology, the first sequence is at least about 75%, preferably at least about 85%, and more preferably at least about 95% identical to the second nucleotide sequence.

The amino acid sequence of a first protein is considered to be homologous to that of a second protein if the amino acid sequence of the first protein shares at least about 20% amino acid sequence identity, preferably at least about 40% identity, and more preferably at least about 60% identity, with the sequence of the second protein. In the case of proteins having high homology, the amino acid sequence of the first protein shares at least about 75% sequence identity, preferably at least about 85% identity, and more preferably at least about 95% identity, with the amino acid sequence of the second protein.

In order to compare a first amino acid or nucleic acid sequence to a second amino acid or nucleic acid sequence for the purpose of determining homology, the sequences are aligned so as to maximize the number of identical amino acid residues or nucleotides. The sequences of highly homologous proteins and nucleic acid molecules can usually be aligned by visual inspection. If visual inspection is insufficient, the nucleic acid molecules may be aligned in accordance with the methods described by George, D. G. et al., in *Macromolecular Sequencing and Synthesis, Selected Methods and Applications*, pages 127–149, Alan R. Liss, Inc. (1988), such as formula 4 at page 137 using a match score of 1, a mismatch score of 0, and a gap penalty of −1.

The invention includes nucleic acids that hybridize to SEQ ID NO:2, SEQ ID NO:5 or SEQ ID NO:6, a fragment of SEQ ID NO:2, SEQ ID NO:5 or SEQ ID NO:6, a complement of SEQ ID NO:2, SEQ ID NO:5 or SEQ ID NO:6, or a complement of a fragment of SEQ ID NO:2, SEQ ID NO:5 or SEQ ID NO:6, under highly stringent conditions. Also included in the invention are proteins that are encoded by nucleic acid molecules that hybridize under highly stringent conditions to a sequence complementary to SEQ ID NO:2, SEQ ID NO:5 or SEQ ID NO:6.

The term "stringent conditions," as used herein, is equivalent to "highly stringent conditions" and "high stringency." These terms are used interchangeably in the art.

Highly stringent conditions are defined in a number of ways. In one definition, stringent conditions are selected to be about 25° C. lower than the thermal melting point ($T_m$) for DNA or RNA hybrids longer than 70 bases, and 5° C. lower than the $T_m$ for shorter oligonucleotides (11–70 bases long). The $T_m$ is the temperature (under defined ionic strength and pH) at which 50% of the target sequence hybridizes to a perfectly matched sequence. Typical stringent conditions are those in which the salt concentration is about 0.02 M at pH 7.0 and the temperature is calculated as described below.

The following equations are used to calculate the $T_m$ of the following hybrids at pH 7.0: For DNA hybrids of more than 70 nucleotides: $T_m=81.5°$ C.$+16.6$ log$[M^+]+41(\%$ G+C$)-0.63(\%$ formamide$)-(600/L)$. For DNA: RNA hybrids of more than 70 nucleotides: $T_m=79.8°$ C.$+18.5$ log$[M^+]+58.4(\%$ G+C$)+11.8(\%$G+C$)^2+0.5(\%$ formamide$)-820/L$. For DNA or RNA hybrids of 14–70 bases: $T_m=81.5°$ C.$+16.6$ log$[M^+]+41(\%$ G+C$)-600/L$. For DNA or RNA hybrids of 11–27 bases (based on 1 M Na$^+$ and in the complete absence of organic solvents): $T_m=4(\%$ G+C$)+2(\%$ A+T$)$.

Where $T_m$=thermal melting temperature;

% G+C=percentage of total guanine and cytosine bases in the DNA, usually 30%–75% (50% is ideal), and expressed as a mole fraction;

$[M^+]$=log of the monovalent cation concentration, usually sodium, expressed in molarity in the range of 0.01 M to 0.4 M; and L=length of the hybrid in base pairs;

% A+T=percentage of total adenine and thymine bases in the DNA and expressed as a mole fraction.

"Stringent conditions," in referring to homology or substantial similarity in the hybridization context, can be combined conditions of salt, temperature, organic solvents or other parameters that are typically known to control hybridization reactions. The combination of parameters is more important than the measure of any single parameter. If incompletely complementary sequences recognize each other under highly stringency conditions, then these sequences hybridize under conditions of high stringency. See U.S. Pat. No. 5,786,210; Wetmur and Davidson J. Mol. Biol. 31, 349–370 (1968). Control of hybridization conditions, and the relationships between hybridization conditions and degree of homology are understood by those skilled in the art. See, e.g., Sambrook J, Fritsch E F, and Maniatis T, Molecular Cloning. A Laboratory Manual, 2d ed., Cold Spring Harbor Laboratory, Cold Spring Harbor (1989).

Further examples of stringent conditions can be found in U.S. Pat. No. 5,789,550 to Goeddel et al. (1998). The description of stringent conditions in U.S. Pat. No. 5,789,550 is herein incorporated by reference. "Stringent conditions" can be provided in a variety of ways such as overnight incubation at 42° C. in a solution comprising: 20% formamide, 5×SSC (150 MM NaCl, 15 mM trisodium citrate), 50 mM sodium phosphate (pH 7.6), 5× Denhardt's solution, 10% dextran sulfate, and 20 µg/ml denatured, sheared salmon sperm DNA. Alternatively, the stringent conditions are characterized by a hybridization buffer comprising 30% formamide in 5×SSPE (0.18 M NaCl, 0.01 M NaPO$_4$, pH 7.7, 0.0001 M EDTA) buffer at a temperature of 42° C., and subsequent washing at 42° C. with 0.2×SSPE. Preferably, stringent conditions involve the use of a hybridization buffer comprising 50% formamide in 5×SSPE at a temperature of 42° C. and washing at the same temperature with 0.2×SSPE. Other stringent conditions known in the art can also be used.

IKKα-ΔLH or IKKα-ΔCm activity or function can be determined by assays well known in the art. A kinase assay using Glutathione S-transferase-IκB (1–62) as a substrate is described below. Glutathione S-transferase-IκB (1–62) is a recombinant fusion protein containing a 62 amino acid N-terminal fragment of IκBα. The IκBα (1–62) fragment only contains two phophoaccepting serines at positions 32 and 36. Other suitable assays are described, for example, in U.S. Pat. No. 5,776,717 to Cao. The description of IκB kinase assays in U.S. Pat. No. 5,776,717 is herein incorporated by reference.

The proteins and variants of the proteins can be prepared by methods known in the art. Such methods include isolating the protein directly from cells, and synthesizing the protein chemically from individual amino acids. Preferably, the proteins of the invention can be prepared by providing DNA that encodes the protein, amplifying or cloning the DNA, expressing the DNA in a suitable host, and harvesting the protein.

DNA encoding the proteins of the invention can be synthesized or isolated. The DNA of the invention can be synthesized chemically from the four nucleotides in whole or in part by methods known in the art. Such methods include those described by Caruthers M H, Science 230:281–285 (1985). DNA can also be synthesized by preparing overlapping double-stranded oligonucleotides, filling in the gaps, and ligating the ends together. See, generally, Sambrook et al. (1989) and Glover D M and Hames B D, eds., DNA Cloning, 2d ed., Vols. 1–4, IRL Press, Oxford (1995).

DNA expressing functional homologs of the protein can be prepared from wild-type DNA by site-directed mutagenesis. See, for example, Zoller and Smith, Nucleic Acids Res 10:6487–6500 (1982); Zoller, Methods Enzymol 100:468–500 (1983); Zoller, DNA 3(6):479–488 (1984); and McPherson, ed., Directed Mutagenesis. *A Practical Approach*, IRL Press, Oxford (1991).

DNA encoding the protein of the invention can be isolated from different species by using SEQ ID NO:2, SEQ ID NO:5 or SEQ ID NO:6 to prepare one or more oligonucleotide probes. The probe is labeled and used to screen a genomic or cDNA library in a suitable vector, such as phage lambda. The homology between the DNA of the species being screened and that of mouse is taken into account in determining the conditions of hybridization. The cDNA library may be prepared from mRNA by known methods, such as those described in Gubler and Hoffman, Gene 25, 263–270 (1983). Oligonucleotide probes can be used to screen cDNA libraries from different species and tissues. The oligonucleotide probe should be labeled so that it can be detected upon hybridization to DNA in the library being screened. These methods are well known in the art.

The DNA isolated is sequenced, and the sequence used to prepare additional oligonucleotide probes. This procedure may be repeated to obtain overlapping fragments until a complete open reading frame is produced.

The nucleic acids of the invention may be amplified by methods known in the art. One suitable method is the polymerase chain reaction (PCR) method described by Saiki et al., Science 239:487 (1988), Mullis et al in U.S. Pat. No. 4,683,195 and by Sambrook et al. (1989). It is convenient to amplify the clones in the lambda-gt10 or lambda-gt11 vectors using lambda-gt10 or lambda-gt11-specific oligomers as the amplimers (available from Clontech, Palo Alto, Calif.). Other amplification procedures that are well known in the art such as ligase chain reaction (LCR), Repair Chain Reaction (RCR), and PCR oligonucleotide ligation assay (PCR-OLA) can also be used to amplify the nucleic acids of the invention.

DNA encoding the proteins of the invention, or unique fragments thereof, may also be cloned in a suitable host cell and expressed by methods well known in the art. The DNA and protein may be recovered from the host cell. See, generally, Sambrook et al. (1989), for methods relating to the manufacture and manipulation of nucleic acids. The entire gene or additional fragments of the gene can be isolated by using the known DNA sequence or a fragment thereof as a probe. To do so, restriction fragments from a genomic or cDNA library may be identified by Southern hybridization using labeled oligonucleotide probes derived from SEQ ID NO:2, SEQ ID NO:5 or SEQ ID NO:6.

The amplified or cloned DNA can be expressed in a suitable expression vector by methods known in the art. See, generally, Sambrook et al. (1989).

A variety of expression vectors and host cell systems can be used. These include, for example, microorganisms such as bacteria transformed with recombinant bacteriophage DNA, plasmid DNA, or cosmid DNA containing the IKKα-ΔLH or IKKα-ΔCm coding region. Other expression vectors and host cell systems that can be used include yeast transformed with recombinant yeast expression vectors containing the IKKα-ΔLH or IKKα-ΔCm coding sequence, insect cells infected with recombinant virus expression vectors containing the IKKα-ΔLH or IKKα-ΔCm coding sequence, plant cells infected with recombinant virus expression vectors containing the IKKα-ΔLH or IKKα-ΔCm coding sequence, or animal cells infected with recombinant virus expression vectors (e.g., retroviruses, adenovirus, vaccinia virus) containing the IKKα-ΔLH or IKKα-ΔCm coding sequence.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X776, *E. coli* X2282, *E. coil* DHI, and *E. coli* MRC1, Pseudomonas sp., Bacillus sp., such as *B. subtilis*, and Streptomyces sp. Suitable eukaryotic cells include yeasts and other fungi, insect, animal cells, such as COS cells and CHO cells, human cells and plant cells in tissue culture.

Preferably, IKKα-ΔLH or IKKα-ΔCm is expressed using baculoviral vectors in insect cells. In general, the transformation of insect cells and production of foreign proteins therein is disclosed in Guarino et al., U.S. Pat. No. 5,162,222.

Proteins can be isolated from a solubilized fraction by standard methods. Some suitable methods include precipitation and liquid chromatographic protocols such as ion exchange, hydrophobic interaction, and gel filtration. See, for example, *Methods Enzymol* (*Guide to Protein Chemistry*, Deutscher, ed., Section VII) pp. 182:309 (1990) and Scopes, *Protein Purification*, Springer-Verlag, New York (1987), which are herein incorporated by reference.

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce. Mixtures of proteins can be separated by, for example, SDS-PAGE in accordance with the method of Laemmli, Nature 227:680–685 (1970). Such methods are well known in the art.

The proteins of the invention can also be chemically synthesized by methods known in the art. Suitable methods for synthesizing proteins are described by Stuart and Young, *Solid Phase Peptide Synthesis*, 2d ed., Pierce Chemical Company (1984).

Also included in the invention are antibodies that bind to epitopes found on IKKα-ΔLH that differ from IKKα and IKKβ due to differences in the protein structure because of the lack of a helix-loop-helix region and leucine zipper region. An "antibody" in accordance with the present specification is defined broadly as a protein that binds specifically to an epitope. The antibodies of the invention can be monoclonal antibodies, polyclonal antibodies, chimerized antibodies, humanized antibodies, single chain antibodies, or a fragment. For use in in vivo applications with human subjects, the antibody is preferably chimerized or humanized, containing an antigen binding region from, e.g., a rodent, with the bulk of the antibody replaced with sequences derived from human immunoglobulin.

Antibodies further include recombinant polyclonal or monoclonal Fab fragments prepared in accordance with the method of Huse et al., Science 246:1275–1281 (1989).

Polyclonal antibodies are isolated from mammals that have been inoculated with the protein or a functional analog in accordance with methods known in the art. Briefly, polyclonal antibodies may be produced by injecting a host mammal, such as a rabbit, mouse, rat, or goat, with the protein or a fragment thereof capable of producing antibodies that distinguish between mutant and wild-type protein. The peptide or peptide fragment injected may contain the wild-type sequence or the mutant sequence. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein, Nature 256:495–497 (1975) and by Campbell, in Burdon et al., eds, *Laboratory Techniques in Biochemistry and Molecular Biology*, Vol. 13, Elsevier Science Publishers, Amsterdam (1985); as well as the recombinant DNA method described by Huse et al., Science 246:1275–1281 (1989).

To produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein (1975). See also Campbell (1985). To be useful, a peptide fragment must contain sufficient amino acid residues to define the epitope of the molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule.

Methods for making chimeric and humanized antibodies are also known in the art. For example, antibodies can be engineered using genetic techniques to produce chimeric antibodies including protein components from two or more species.

For example, methods for making chimeric antibodies include those described in U.S. patents by Boss (Celltech) and by Cabilly (Genentech). See U.S. Pat. Nos. 4,816,397 and 4,816,567, respectively. Methods for making humanized antibodies are described, for example, in Winter, U.S. Pat. No. 5,225,539, Co et al., Nature 351, 501–502 (1992); Queen et al., Proc. Natl. Acad. Sci. 86, 10029–1003 (1989) and Rodrigues et al., Int. J. Cancer, Supplement 7, 45–50 (1992).

Methods are also known for inducing expression of engineered antibodies in various cell types, such as mammalian and microbial cell types. Numerous techniques for preparing engineered antibodies are described, for example, in Owens and Young, "The genetic engineering of monoclonal antibodies," J. Immunol. Meth. 168:149–165 (1994).

Methods for making single chain antibodies are also known in the art. Some suitable examples include those described by Wels et al. in European patent application 502 812 and Int. J. Cancer 60, 137–144 (1995).

Assays for directly detecting the presence of IKK$\alpha$-$\Delta$LH or IKK$\alpha$-$\Delta$Cm with antibodies follow known formats, such as, fluorescent activated flow cytometry, fluorescent microscopy, and immuno-electron microscopy. Moreover, assays for detecting the presence of proteins with antibodies have been previously described and follow known formats, such as standard blot and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

Suitable assays are known in the art, such as the standard ELISA protocol described by R. H. Kenneth, "Enzyme-linked antibody assay with cells attached to polyvinyl chloride plates" in Kenneth et al., *Monoclonal Antibodies*, Plenum Press, New York, pp. 376 et seq. (1981).

In another embodiment of the invention, the invention includes methods for screening for agents that modulate I$\kappa$B phosphorylation by I$\kappa$B kinases. The method involves screening for compounds, or agents, which modulate I$\kappa$B phosphorylation by the I$\kappa$B kinases of the invention, such as, for example, IKK$\alpha$-$\Delta$LH or IKK$\alpha$-$\Delta$Cm. Because, unlike other I$\kappa$B kinases, IKK$\alpha$-$\Delta$LH and IKK$\alpha$-$\Delta$Cm can function as a monomer, screens for modulators of kinase activity can be targeted to a minimal IKK$\alpha$ functional domain. Also, because IKK$\beta$ is not required for the functional activity of the proteins of the invention, only one kinase needs to be present in the kinase assay. Moreover, since IKK$\alpha$-$\Delta$LH and IKK$\alpha$-$\Delta$Cm lack both the helix-loop-helix domain and the leucine zipper region, drugs which inhibit IKK$\alpha$-$\Delta$LH and IKK$\alpha$-$\Delta$Cm are specifically directed to the kinases' catalytic domain, thereby providing an improved specificity of action. These are unique advantages provided by the invention that simplify the analysis and search for modulating agents that are useful therapeutics.

Modulation of I$\kappa$B phosphorylation can be either inhibition or an increase in phosphorylation (induction) at an I$\kappa$B phosphorylation site. Therefore, modulating agents are either inhibitors or inducers of I$\kappa$B phosphorylation by I$\kappa$B kinases. Inhibitors are useful as immunosuppressants or antiinflammatory agents. Inducers can be used, for example, to stimulate immune responses in immunosupressed patients.

Screening for agents that modulate I$\kappa$B phosphorylation by the I$\kappa$B kinases of the invention comprises the steps of incubating a mixture of the kinase, an I$\kappa$B phosphorylation site, and a candidate modulating agent and detecting the agent-biased phosphorylation level of the phosphorylation site by the kinase. The agent-biased phosphorylation level is then compared with an agent-independent phosphorylation level determined in the absence of the modulating agent. In this way, candidate modulating agents can be identified and assessed for their potential effectiveness as therapeutic agents.

A significant difference between the agent-biased phosphorylation level and the agent-independent phosphorylation level indicates that the agent modulates I$\kappa$B phosphorylation.

A significant difference, as used herein, means that at least 10% difference is observed, more preferably at least 50%, and most preferably, at least 80%. An agent that modulates I$\kappa$B phosphorylation by I$\kappa$B kinases can be used, or developed, for therapeutic purposes.

Candidate modulating agents can be selected from small molecules, peptides, and proteins. Small molecules are desirable as therapeutic agents since they are more likely to be permeable to cells and are less susceptible to degradation than are biological macromolecules. Small molecules include, but are not limited to, organic or inorganic compounds of molecular weight less than 700 and peptides of molecular weight less than 10 kDa. The organic or inorganic compounds can be synthetic or natural. Proteins, such as antibodies, and peptides having a molecular weight greater than 10 kDa can also be candidate modulating agents. The methods of the invention are amenable to high-throughput screening of chemical libraries and are especially useful for identifying small molecule drug candidates.

I$\kappa$B phosphorylation sites include the serine residues of I$\kappa$Bs that are phosphorylated by I$\kappa$B kinases. In the case of I$\kappa$B$\alpha$, the phosphorylation sites include serine 32 and/or serine 36. However, other I$\kappa$B phosphorylation sites such as serine 19 and/or serine 23 of IκBβ can also be used. In addition, other IκB phosphorylation sites present on different variants of IκB, alleles of IκB, and fragments of IκB proteins that maintain the structural integrity of IκB phosphorylation sites, can be used.

The agent-biased phosphorylation level is the phosphorylation observed in the presence of a candidate modulating agent and the agent-independent phosphorylation level is the phosphorylation level in the absence of the candidate modulating agent.

The assay mixture can additionally comprise a variety of other components such as salts, buffers, carrier proteins (e.g. albumin), detergents, protease inhibitors, etc., that may be used to improve the efficiency of the assay.

Any phosphorylation assay (kinase assay) known in the art can be used with this embodiment of the invention. For example, the phosphorylation assays described in U.S. Pat. No. 5,776,717 to Cao, with appropriate modifications, can be used. U.S. Pat. No. 5,776,717 to Cao is herein incorporated by reference for its kinase assay disclosure. A preferred kinase assay uses GST-fusion proteins of appropriate IκB substrates. GST-fusions are described in Smith and Johnson, Gene 67, 31–40 (1988).

EXAMPLES

Abbreviations

AKAP, A-kinase anchoring protein; CHUK, conserved helix-loop-helix ubiquitous kinase; GST, glutathione S-transferase; HA, hemagglutinin; IKK, I B kinase; IL, Interleukin; MEKK-1, mitogen-activated protein kinase/ERK kinase kinase-1; NIK, NF-kB-inducing kinase; RT, reverse transcriptase; TNF, tumor necrosis factor: TRAF, tumor necrosis factor receptor-associated factor.

Materials and Methods cDNA library screening. An MPC-11 mouse myeloma cDNA library was prepared in λ-ZapII(XR) (Stratagene Inc) and screened with IKKα/CIUK specific probes along with a BALB/c lung λ-Zap II library (Stratagene Inc.) and a BXSB mouse spleen λ-gt-10 library as previously described (Connelly and Marcu, 1995)

Plasmids. Murine IKKα]was amplified by the polymerase chain reaction (PCR) from pBluescript KS(+) (Stratagene) and cloned into pcDNA3.1 (Invitrogen, CA) in frame with a C-terminal HA epitope tag to generate pcDNA-IKKα-HA. Myc-NIK, IKKα-T7, NF-κB-dependent luciferase and RSV-βgal reporter plasmids were all as previously described (Geleziunas et al., 1998). IKKα-ΔLH and IKKα-ΔH were cloned by PCR from pBluescript KS(+) in frame with a carboxy-terminal V5 epitope tag in pcDNA3.1/V5/His-TOPO as described by the manufacturer (Invitrogen Inc.). IKKα-αCm (amino acids 1–451 of lKKα), a recombinant derivative of IKKα-ΔLH lacking its unique 20 amino acid C-terminal tail, was also cloned by PCR in frame with the C-terminal V5 epitope of pcDNA3.1/V5/His-TOPO. IKKβ-ΔCm (amino-acids 1–454 and structurally analogous to IKKα-ΔCm) was amplified from a human IKKβ construct with primer pairs 5'-TAGAGAACCGCACTGCTTAC TGGCT-3' (SEQ ID NO: 7) and 5-GGCGGCTC GCTGTCCCTGCT-3' (SEQ ID NO: 8) into pcDNA3.1/V5/His-TOPO. IKKα-KΔm (amino acids 1–345, specifying the kinase catalytic domain) was amplified from a human IKKα expression vector with primer pairs 5'-CGATGGACTACAAAGACGA-3' (SEQ ID NO: 9) and 5'-CAAGTTTCACGCTCAATACGAG-3' (SEQ ID NO: 10) into pcDNA3.1/V5/His-TOPO. A complete NEMO coding sequence was cloned by RT-PCR with primer pairs 5'-ACACTGTCCTGTTGGATGAA-3' (SEQ ID NO: 11) and 5'-CTCTATGCATCCATGACAT-3' (SEQ ID NO: 12) from the EL4 murine T cell line. Two independent, 1.3 κB full length clones yielded a sequence identical to that previously published. Complementation cloning of NEMO, a component of the IκB kinase complex essential for NF-κB activation, with one base change (C,38,T) converting amino acid #13 from threonine to methionine. The NEMO cDNA was subcloned into pcDNA3.1(+) in frame with a carboxy-terminal Myc-epitope tag coding sequence. Δ-NEMO (an N-terminal truncation, leaving amino-acids 235–419) was amplified from a hill length cDNA clone with primer pairs 5'-CCAACTCTTAGACTACGACAG-3' (SEQ ID NO: 13) and 5'-CTCTATGACCTCCATGACAT-3' SEQ ID NO: 14), initially cloned into the TA cloning vector pCR2.1 (Invitrogen) and subsequently released by EcoR1 digestion and re-cloned in-frame with an N-terminal M45 epitope tag into a CMV promoter driven mammalian expression vector.

Cells and Culture Conditions. Human Embryonic Kidney cells (HEK293) and HeLa cells were cultivated in Dulbecco's modified Eagle's medium (DMEM) (Gibco/BRL) containing 10% fetal bovine serum, penicillin (50 U/ml) and streptomycin sulfate (50 μg/ml). Explanted BALB/c thymocytes were cultured in RPMI 1640 media supplemented with penicillin, streptomycin and 10% fetal bovine serum (Hyclone Inc.). In some experiments, T cell cultures were stimulated with either 10 ng/ml of the phorbol ester PMA (Sigma) plus 100 ng/ml of the calcium ionophore A23187 (Calbiochem) or 100 ng/ml of the T cell mitogen ConA (Amersham Pharmacia Biotech.) for 7 days prior to harvesting total cellular RNAs.

Antibodies and recombinant proteins. Anti-T7 and Anti-V5 antibodies were obtained from Novagen and Invitrogen respectively and recombinant TNF-α from GIBCO-BRL. GST-IκBα (1–62) was produced and purified by standard procedures. Anti-Flag tag antibodies (M2) were purchased from Eastman Kodak Company (Hollywood, Calif.). Anti-HA tag mouse monoclonal antibody 12CA5 was obtained from Berkeley Antibody Company (Richmond, Calif.).

Luciferase reporter assays. 293 cells were seeded in 6-well plates at a density of $6 \times 10^5$ cells per well the day before transfection. DNA transfections were performed by the calcium phosphate precipitation method with up to 4%g of expression plasmid, 0.5 μg of NF-κB luciferase reporter plasmid and 0.25 μg of RSV-Gal plasmid which served as an internal transfection efficiency control. Total DNA concentrations in each transfection were kept constant by supplementing with empty pcDNA3.1 expression vector. Twenty four hours post-transfection, cells were stimulated where appropriate with TNF (10 ng/ml) for 6 h prior to cell lysis. Luciferase and β-Galactosidase activities were quantitated with a Promega Inc. (Madison, Wis.) assay kit as recommended by the provider.

RT-PCRs of IKKα/CHUK isoforms. IKKα/CHUK, IKKα-ΔH and IKKα-ΔLH(a & b) transcripts were distinguished by RT-PCR assays. Total cellular RNAs (5 μg) were extracted from various cell lines and tissues with triazol reagent (Roche Molecular Biochemicals) and reverse transcribed into cDNAs in a 20 μl reverse transcriptase reaction. RNAs were preincubated with 10 pmoles of an anchored oligo dT primer 5'-AGCTCCGGAATTCGGTTTTTTTTTTTVN-3' (SEQ ID NO: 15) in up to 12 μl of sterile, distilled H₂O at 70° C. for 10 mm and quick chilled on ice. After a brief centrifugation, the reverse transcriptase reactions were performed with a SUPERSCRIPT II RT kit as recommended by the manufacturer (BRL Life Tech.). Briefly the reaction was initially supplemented with 4 μl of 5X first strand buffer (BRL Life Tech.), 2 μl 0.1 M DTT and 1 μd of a 10 mM mixture of all four dNTPs. After a second pre-incubation at 42° C. for 2 min., 1 μl (200 units) of SUBPERSCRIPT II (BRL Life Tech.), a mutant form of Moloney Murine Leukemia virus reverse transcriptase lacking RNase activity, was added, and the reaction allowed to proceed at 42° C. for 50 mm. followed by inactivation at 70° C. for 15 mm. The resultant cDNAs were directly used in 40 μl PCR reactions containing 20 pmoles of each primer, 50 mM KCl, 10 mM Tris-HCl (pH 9.0), 0.01% Triton X-100, 1.5 mM MgCl$_2$, and 2 units of Taq polymerase (Promega Inc.). All RT-PCRs were performed with a 5' amplimer present in all forms of IKKα/CHUK (α5'-ACCATTTGCATCCAGAAGTTTATC-3' (SEQ ID NO: 16), 1241–1264 bp) and one of four 3' primers: (1) β: 5'-CAGGAGGTCTGTGCTTTAGCTG-3' (SEQ ID NO: 17), 1761–1782 bp in all forms of IKKα/CHUK, (2) δ: 5'-TGCTCAGGTGACCAAACAGCT-3' (SEQ ID NO: 18), 1861–1881 bp of IKKα/CHUK and CHUK(ΔLHa), (3) γ: 5'-GCAAAAAGAATACCAAAACAGGAT-3' (SEQ ID NO: 19), 1879–1902 bp of IKKα-ΔH and IKKα-ΔLHb and (4) ε: 5'-GATAACCAATGACACCAACCTC-3' (SEQ ID NO: 20), 1620–1641 bp in all forms of IKKα/CHUK. In some PCRs (FIGS. 1 and 3), 20 pmoles of 5 ' a were mixed with 10 pmoles each of δ and γ PCRs were submitted to a hot start protocol (AmpliWax Gems, Perkin-Elmer Inc.) followed by a 4 min. preincubation at 94° C. and 26 cycles (30 sec. at 94° C., 1 mm at 62° C. and 1 mm at 72° C.). Reaction products were resolved by 6% PAGE.

Immune complex kinase assays. HEK293 cells (2.5×10 cells in 10 cm plates) were transfected with 10 μg of kinase expression plasmid by the calcium phosphate method and stimulated 24 h later in DMEM with appropriate agonist at 37° C. for the times indicated. Cells were washed with ice cold PBS and lysed with Triton X-100 lysis buffer (50 mM Tris-HCl, pH 7.5, 100 mM NaCl, 50 mM NaF, 5 mM EDTA, 40 mM β-glycerophosphate, 200 μM sodium orthovanadate, 10$^{-4}$M phenylmethyl-sulfonyl fluoride, 1 mg/ml leupeptin, 1 μM pepstatin A, 1% Triton X-100). Proteins from lysates (500 μg) were incubated with specific anti-HA (12CA5) or V5 epitope (Invitrogen Inc.) antibodies preadsorbed to protein A-Sepharose coated beads for 2 h at 4° C. Immune complexes were washed three times with Triton X-100 lysis buffer and twice with kinase assay buffer (20 mM HEPES, pH 7.4, 20 mM MgCl$_2$, 1 mM dithiothreitol, 10 mM p-nitrophenylphosphate). IKKA activity was assayed by resuspending the final pellet in 40 μl of kinase buffer containing 50 μM of [α-$^{32}$P] ATP (5000 c.p.m./pmol) (Amersham) and 0.25 mg/ml of GST-IκBα(1–62). The reaction was incubated for 10 min at 30° C. and stopped with Laemmli sample buffer. Samples were resolved on SDS-PAGE (10%) and phosphorylation determined by exposure in a phosphorimager (Molecular Dynamics).

Immunoblotting. Cell lysates were prepared in Triton X-100 lysis buffer as described above for the kinase assays. Proteins in cellular lysates were separated on 7.5% SDS-PAGE and electroblotted onto Hybond-C Extra membranes (Amersham). Protein blots were exposed to specific primary antibodies followed by horseradish peroxidase-conjugated 2° antibodies which were subsequently detected with enhanced chemiluminescence (ECL) immunodetection (Amersham) by standard procedures.

In-vitro translation. Constructs in pcDNA3.1 were translated in a Promega rabbit reticulocyte in-vitro translation kit either with $^{35}$S-methionine (Amersham) or with unlabeled methionine as per the manufacturer's instructions.

Protein determinations. Proteins were quantitated with a bicinchoninic acid protein assay kit (Pierce, Rockford, Ill.) using bovine serum albumin as a standard.

Example 1

Structural Comparisons of Murine IKKα/CHUK, IKKα-ΔH and IKKα-ΔLH(a & b) cDNA Clones Screening of several murine cDNA libraries (BALB/c lung, BXSB spleen and MPC-11 mouse myeloma) with IKKα/CHUK specific probes produced multiple isolates of three IKKα/CHUK cDNAs with overlapping and different structural features. Thus, alternative IKKα/CHUK transcripts are expressed by different cell types. As shown in FIG. 1, IKKα-ΔH is a unique isoform which is identical to IKKα/CHUK until residue 576 (nucleotide 1782) whereupon the former cDNA has a novel 3' non-coding sequence. The presence of a translation stop, after eight additional codons in IKKα-ΔH, truncates the polypeptide chain twenty four amino acids upstream of the H-L-H domain replacing the remainder of the protein with a short, eight amino acid carboxy-terminal extension. In addition, the alternative 3' non-coding sequence (NCS) in IKKα-ΔH exhibited significant homology to the sequence of the H-L-H domain indicating that this 3'NCS is likely specified by an alternative splice to a duplicated exon which has undergone extensive sequence divergence. IKKα-ΔLHa and IKKα-ΔLHb are two other isoforms of the full length IKKα/CHUK transcript both bearing the same 152 bp deletion of nucleotides 1408–1559. The latter deletion excises the LZip domain downstream of residue 451 and then switches the reading frame to generate a translation stop codon after adding on a short twenty amino acid carboxy-terminal tail (FIG. 1). The remainder of the IKKα-ΔLHa mRNA is structurally identical to full length IKKα/CHUK mRNA while the related IKKα-ΔLHb mRNA isoform possesses the same 3'NCS as IKKα-ΔH again at nucleotide 1782 (FIG. 1).

Examples 2 and 3:

Unlike IKKα/CHUK, IKKα-ΔH and IKKα-ΔLH(a & b) are differentially expressed

RT-PCR was employed to investigate the expression patterns of the four IKKα/CHUK transcripts in a variety of cell types and normal murine tissues. An RT-PCR strategy was designed to co-amplify all four isoforms and to distinguish their PCR products on a 6% polyacrylamide gel. A 5' Pan IKKα/CHUK amplimer, which is conserved in all four sequences (nucleotides 1241–1264, see location of α primer in FIG. 1), was paired with four different 3' primers: (1) 3' Pan IKKα/CHUK 1761–1782, which is between the LZip and H-L-H domains and present in all four sequences, (see β in FIG. 1); (2) 3' IKKα 1861–1881 in the H-L-H domain (see 6 in FIG. 1); (3) 3' IKKα-ΔH 1879–1902 in the 3'NCS of IKKα-ΔH and IKKα-ΔLHb (see γ in FIG. 1) and (4) 3' IKKα 1620–1641, which like primer β is between the LZip and H-L-H domains and present in all four sequences (see ε in FIG. 1). PCR amplification of anchored oligo dT primed cDNAs with a vs δ produced IKKα/CHUK and IKKα-ΔLHa specific bands of 640 and 488 bp (see FIGS. 1 and 2). RT-PCR performed with a vs γ yielded IKKα-ΔH and IKKα-ΔLHb bands of 661 and 509 bp (also in FIGS. 1 and 2). Amplifications with a mixture of all three produced all four bands with similar relative intensities (see FIGS. 1 and 2B). The identities of the four bands were confirmed by restriction digestion and DNA sequencing (data not shown). The sizes of the IKKα-ΔH and IKKα-ΔLHa bands were 21 bp larger than the IKKα/CHUK, and IKKα-ΔLHb species since the distances between α and δ vs α and γ differed by 21 bp. PCRs performed with increasing doses of cDNA templates indicated that the relative intensities of the individual bands in each amplification were close approximations of the relative quantities of their mRNAs (see cDNA dose response analyses of thymus, brain and 70Z3 lines in FIGS. 1 and 2B). To independently determine the relative amounts of the IKKα-ΔLH(a & b) isoforms in comparison to IKKα/CHUK and IKKα-ΔH, RT-PCRs were performed with primer pairs conserved in all four isoforms (IKKα 5' and 3' Pan primers) which flanked the site of the 152 bp (LZip) deletion in the IKKα-ΔLH(a & b) isoforms (see location of primers α, β and ε in FIGS. 1 & 3). As shown in FIG. 3, the latter results are in good agreement with the RT-PCRs shown in FIGS. 1 and 2.

IKKα/CHUK is the major mRNA species in most cell types and tissues while the three new mRNA isoforms are differentially expressed. Numerous experiments with a variety of murine tissue samples reveals that the relative expression of IKKα-ΔH in comparison to full length IKKα follows a rank order pattern of brain>thymus>spleen>lung=liver>heart where IKKα-ΔH predominates over IKKα in the brain but is only ~5% of IKKα in the heart (FIGS. 1, 3A, 3B and data not shown). In a larger survey of a variety of established cell lines, IKKα-ΔH varied from being almost undetectable to about 20% of IKKα (FIG. 2A and data not shown). In contrast, the IKKα-ΔLH isoforms were more apparent in thymus (~30% of IKKα) than in all other tissues (10–20% of IKKα) except for the brain where IKKα and IKKα-ΔLHa were comparably expressed (FIGS. 2A, 2B and 3A and data not shown). In established cell lines, the IKKα-ΔLH isoforms were more strongly expressed in a mature T cell lymphoma (EL4) (at least 50% of all forms of IKKα) and a monocytic leukemia (FDJ2) (~25% of IKKα) than in other cell types (including immature B and T lymphocytes, macrophages, fibroblasts, erythroid and epithelial cells) where they were weakly expressed (see FIGS. 2A and 3A). Interestingly, the IKKα-ΔLH isoforms were differentially enhanced relative to IKKα/CHUK and IKKα-ΔH upon mitogenic co-stimulation of normal T cells with a phorbol ester and a calcium ionophore (PMA and A23187) (FIG. 2A and B) or ConA, a T cell specific lectin (FIG. 3B). Remarkably, the level of the IKKα-ΔLH isoform in PMA+A23187 stimulated T cells became similar to the combined expression of IKKα and IKKα-ΔH (FIG. 3B). The IKKα-ΔLHb isoform tends to predominate over the ΔLHa species except in the stronger expressing EL4 and FDJ2 lines where they accumulate to similar levels. Interestingly, the IKKα-ΔLH isoforms were absent and IKKα-ΔH barely detectable in the parental 70Z3 pre-B line and in its 1.3E2 (ΔNEMO) mutant (FIG. 2B), which has been shown to require NEMO complementation to achieve NF-κB activation, a component of the IkappaB kinase complex essential for NF-kappaB activation. Stimulation of either parental 70Z3 cells or the 1.3E2 mutant with NF-κB inducing stimuli like LPS or PMA also failed to induce the appearance of the smaller IKKα/CHUK isoforms (data not shown).

Example 4

Polypeptides encoded by IKKα-ΔH and IKKα-ΔLH upregulate NF-κB

Activation of NF-κB can be readily detected in transient transfection assays using an NF-κB-dependent reporter gene construct. It was then investigated if the IKKα-ΔH and IKKα-ΔLH proteins, akin to IKKα/CHUK and IKKβ, would activate NF-κB and also potentiate its induction by TNF-α. Co-transfection of IKKα/CHUK leads to a 2 fold increase in TNF-α-stimulated luciferase activity, with little difference in basal NF-κB-driven luciferase activity. As shown in FIGS. 4A and 4B, IKKα-ΔH and IKKα-ΔLH also increase the ability of TNFα to stimulate NF-κB-dependent luciferase activity. As the amount of plasmid encoding each IKKα/CHUK isoform was increased, the TNF-α-induced luciferase activity increased correspondingly in a similar fashion to IKKα (FIG. 4B). Western blot experiments conducted on HEK293 cells transfected with each of the IKKα/CHUK isoforms revealed similar levels of protein expression throughout the dose response analysis (data not shown). Given that each expression vector is limiting at its lowest DNA input but their relative activities remain comparable throughout, these observations are not due to differences attributable to overexpression. Hence in comparison to IKKα/CHUK and IKKβ, the two new smaller IKKα/CHUK isoforms are comparably efficient at potentiating NF-κB activation in response to TNF-α. To verify that the short carboxy-terminal extensions of IKKα-ΔH and IKKα-ΔLH had no unanticipated effects on their activities, the 20 amino acid tail of the smaller IKKα-ΔLH protein was removed. As shown in FIG. 5 and other figures to follow, IKKα-ΔCm, a recombinant form of IKKα-ΔLH, lacking the latter's 20 amino acid tail, was equally capable of enhancing TNF-α stimulation of the NF-κB luciferase reporter. However, further deletion of the remaining 106 amino acids of IKKα separating the amino-proximal kinase and LZip domains inactivated the protein (data not shown and kinase assays in FIG. 5A). IKKβ was constitutively active and could enhance the activity of the NF-κB driven luciferase reporter independent of cytokine stimulation. In sharp contrast to IKKα-ΔCm, IKKβ-ΔCm (amino acids 1–454), a structurally analogous recombinant form of IKKβ (amino acids 1–451), was inactive in the NF-κB reporter assay (FIG. 5A). Thus, IKKα/CHUK, IKKα(ΔH) and IKKα(ΔLH) do not appear to have the same activation constraints as IKKβ.

Example 5

IKKα-ΔH and IKKα-ΔLH are TNF-α Inducible IκBα Kinases

Release of NF-κB from its IκBα inhibitor requires the latter's phosphorylation at serines 32 and 36. To assess the relative abilities of IKKα/CHUK, IKKα-ΔH and IKKα-ΔLH to phosphorylate IκBA in response to TNF-α stimulation, in-vitro kinase assays were performed with GST-IκBα(1–62) as substrate in either anti-HA or anti-V5 immunoprecipitates of HEK293 cells transfected with HA-epitope tagged IKKα/CHUK and IKKα-ΔCm or V5 epitope tagged IKKα-ΔH and IKKα-ΔLH (FIG. 5A). HEK293 cells transiently transfected with each of the IKKα/CHUK isoforms expressed similar amounts of immunodetectable proteins with the expected molecular masses (FIG. 5A, top panel). TNF-α stimulation of HEK293 cells transfected with each IKKα/CHUK isoform resulted in an increase in immunoprecipitatable kinase activity towards GST-IκBα(1–62) (FIG. 5A, bottom panel). However, further truncation of IKKα-ΔCm, by removing its carboxy-terminal 106 amino acids to leave an intact amino-terminal kinase domain (IKKα-KΔm in FIG. 5A), inactivated its TNFα inducible IκBα kinase activity, implying that a block of amino acids residing in between the kinase and LZip domains of IKKα_are part of a cytokine response domain. As anticipated from the NF-κB reporter assay results, all experiments performed with either IKKα-ΔH, IKKα-ΔLH or the recombinant IKKα-ΔCm produced comparable results indicating that neither the LZip domain of IKKα-ΔH nor the short carboxy-terminal extensions of either short isoform had significant effects on IκBα phosphorylation in this assay. Indeed, time course experiments revealed that the activation profiles of IKKα/CHUK and IKKα-ΔCm enzymatic activities in response to TNF-a stimulation were superimposable (FIG. 5B).

Example 6

Unlike IKKα/CHUK and IKKβ, IKKα-ΔH, IKKα-ΔLH and IKKα-ΔCm Polypeptides Fail to Associate with NEMO/IKKγ

Complementation rescue of two cell types which were unresponsive to NF-κB activating agonists, along with purification of the IκB kinase complex resulted in the identification and cloning of NEMO/IKKγ. NEMO/IKKγ appears to be a prerequisite for activation of NF-κB. It does not exhibit enzymatic activity, but possesses a putative leucine zipper domain and several coiled-coil motifs which may mediate interaction with other elements of the NF-κB signaling cascade. In-vitro translated NEMO/IKKγ co-immunoprecipitates with IKKβ and to a lesser extent with IKKα. Co-transfection studies were performed to determine whether each IKKα/CHUK isoform interacted with NEMO/IKKγ. Transient transfection of HEK293 cells with either of IKKβ, IKKα-ΔH, IKKα-ΔLH, IKKα-ΔCm, IKKα/CHUK and NEMO/IKKγ followed by NEMO/IKKγ immunoprecipitation revealed that NEMO/IKKγ associated with both IKKα and IKKβ in-vivo, but failed to associate with the smaller IKKα/CHUK isoforms (FIG. 6) indicating that the H-L-H domain of IKKα was essential for interaction with NEMO/IKKγ.

Example 7

A Carboxy-Truncated Isoform of IKKα (IKKα-ΔCm) Rescues NF-κB Activity from the Inhibitory Effects of a Dominant Negative NEMO/IKKγ Mutant To further elaborate functional distinctions between the activation pathways of IKKα and its truncated isoforms, the effects of a dominant negative mutant of NEMO/IKKγ on the abilities of IKKα/CHUK and IKKα-ΔCm to activate NF-κB in response to TNF-α were assessed. As expected from previous studies, an amino terminally truncated mutant of NEMO/IKKγ inhibited the ability of IKKα/CHUK to stimulate TNF-α inducible NF-κB activation at all dosages (FIG. 7). In contrast IKKα-ΔCm, which lacks the IKKα LZip and H-L-H domains and failed to interact with NEMO/IKKγ in vivo (FIG. 6), efficiently rescues NF-κB induction from the inhibitory effects of the same NEMO/IKKγ mutant (FIG. 7). This and other results presented herein support the view that the carboxy-truncated IKKα isoforms activate NF-κB by an IKKβ and NEMO/IKKγ independent pathway.

What is claimed is:

1. A method of screening for an agent which modulates IκB phosphorylation by an IκB protein kinase, wherein the kinase has a kinase domain and no leucine zipper like α-helix domain, and no helix-loop-helix domain, the method comprising the steps of:

incubating a mixture comprising:
the IκB kinase, and
a candidate modulating agent;

detecting an agent-biased phosphorylation level of the IκB kinase in the presence of the candidate modulating agent;

detecting an agent-independent phosphorylation level of the IκB kinase in the absence of the candidate modulating agent;

comparing the agent-biased phosphorylation level with the agent-independent phosphorylation level; and selecting the candidate modulating agent that exhibits a significant difference between the agent-biased phosphorylation level and the agent-independent phosphorylation level.

2. A method according to claim 1, wherein the IκB is IκBα.

3. A method according to claim 1, wherein the IκB kinase is set forth in SEQ ID NO: 1.

4. A method according to claim 1, wherein the agent inhibits IκB phosphorylation.

5. A method according to claim 1, wherein the agent stimulates IκB phosphorylation.

* * * * *

UNITED STATES PATENT AND TRADEMARK OFFICE
CERTIFICATE OF CORRECTION

PATENT NO. : 6,803,204 B2
DATED : October 12, 2004
INVENTOR(S) : Marcu et al.

It is certified that error appears in the above-identified patent and that said Letters Patent is hereby corrected as shown below:

<u>Column 1</u>,
Line 3, please add -- This invention was made with Government support under Grant No. CA36246 awarded by the National Institutes of Health. The Government has certain rights in the invention. --

Signed and Sealed this

Eleventh Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,803,204 B2
DATED : October 12, 2004
INVENTOR(S) : Marcu et al.

It is certified that error appears in the above-identified patent and that said Letters Patent is hereby corrected as shown below:

Column 9,
Line 34, now reads "$(\%G+C)^2+0.5(\%\ formamide)$" should read -- $(\%\ G+C)^2-0.5(\%\ formamide)$ --.

Column 12,
Lines 6-7, now reads "*E. coli* X776, *E. coli* X2282, *E. coli* DHI"; should read -- *E. coli* X1776, *E. coli* X2282, *E. coli* DHI --.

Column 15,
Line 36, now reads "IKKα/CIUK" should read -- IKKα/CHUK --.
Line 46, now reads "IKKα-ALH" should read -- IKKα-ΔLH --.
Line 48, now reads "carboxy-terminal VS" should read -- carboxy-terminal V5 --.
Line 50, now reads "IKKα-αCm" should read -- IKKα-ΔCm --.
Line 53, now reads "C-terminal VS" should read -- C-terminal V5 --.
Line 57, now reads "and 5-" should read -- and 5-' --.

Column 16,
Line 10, now reads "hill length" should read -- full length --.
Line 12, now reads "SEQ ID NO: 14)" should read -- (SEQ ID NO: 14) --.
Line 41, now reads "4%g" should read -- 4µg --.

Column 17,
Line 1, now reads "SUBPERSCRIPT II" should read -- SUPERSCRIPT II --.
Line 5, now reads "50mm. followed by inactivation at 70°C. for 15 mm" should read -- 50 min. followed by inactivation at 70°C for 15 min. --.
Line 23, now reads "5 ' a" should read -- 5'α --.
Line 24, now reads "δ and γ PCRs" should read -- δ and γ. PCRs --.
Line 27, now reads "1 mm at 62°C. and 1 mm at 72°C." should read -- 1 min at 62°C and 1 min at 72°C --.
Line 29, now reads "(2.5X10 cells" should read -- (2.5 X $10^6$ cells --.

Column 18,
Line 54, now reads "(see 6 in FIG. 1)" should read -- (see δ in FIG. 1) --.
Line 59, now reads "a vs δ" should read -- α vs δ --.
Line 61, now reads "a vs γ" should read -- α vs γ --.

UNITED STATES PATENT AND TRADEMARK OFFICE
CERTIFICATE OF CORRECTION

PATENT NO.   : 6,803,204 B2
DATED        : October 12, 2004
INVENTOR(S)  : Marcu et al.

It is certified that error appears in the above-identified patent and that said Letters Patent is hereby corrected as shown below:

Column 21,
Line 4, now reads "1IκBα" should read -- IκBα --.
Line 7, now reads "TNF-a" should read -- TNF-α --.

Signed and Sealed this

Third Day of May, 2005

JON W. DUDAS
*Director of the United States Patent and Trademark Office*

SEQUENCE LISTING

```
<160> NUMBER OF SEQ ID NOS: 20

<210> SEQ ID NO 1
<211> LENGTH: 451
<212> TYPE: PRT
<213> ORGANISM: homosapiens

<400> SEQUENCE: 1

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Ser Leu Tyr
            20                  25                  30

Gln His Arg Glu Leu Asp Leu Lys Ile Ala Ile Lys Ser Cys Arg Leu
        35                  40                  45

Glu Leu Ser Ser Lys Asn Arg Glu Arg Trp Cys His Glu Ile Gln Ile
    50                  55                  60

Met Lys Lys Leu Asp His Ala Asn Val Val Lys Ala Cys Asp Val Pro
65                  70                  75                  80

Glu Glu Leu Asn Phe Leu Ile Asn Asp Val Pro Leu Leu Ala Met Glu
                85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
        130                 135                 140

Leu Lys Pro Glu Asn Ile Val Leu Gln Asp Val Gly Gly Lys Thr Ile
145                 150                 155                 160
```

-continued

```
His Lys Ile Ile Asp Leu Gly Tyr Ala Lys Asp Val Asp Gln Gly Ser
                165                 170                 175
Leu Cys Thr Ser Phe Val Gly Thr Leu Gln Tyr Leu Ala Pro Glu Leu
            180                 185                 190
Phe Glu Asn Lys Pro Tyr Thr Ala Thr Val Asp Tyr Trp Ser Phe Gly
        195                 200                 205
Thr Met Val Phe Glu Cys Ile Ala Gly Tyr Arg Pro Phe Leu His His
    210                 215                 220
Leu Gln Pro Phe Thr Trp His Glu Lys Ile Lys Lys Asp Pro Lys
225                 230                 235                 240
Cys Ile Phe Ala Cys Glu Glu Met Thr Gly Glu Val Arg Phe Ser Ser
                245                 250                 255
His Leu Pro Gln Pro Asn Ser Leu Cys Ser Leu Ile Val Glu Pro Met
            260                 265                 270
Glu Ser Trp Leu Gln Leu Met Leu Asn Trp Asp Pro Gln Gln Arg Gly
        275                 280                 285
Gly Pro Ile Asp Leu Thr Leu Lys Gln Pro Arg Cys Phe Ala Leu Met
    290                 295                 300
Asp His Ile Leu Asn Leu Lys Ile Val His Ile Leu Asn Met Thr Ser
305                 310                 315                 320
Ala Lys Ile Ile Ser Phe Leu Pro Cys Asp Glu Ser Leu His Ser
                325                 330                 335
Leu Gln Ser Arg Ile Glu Arg Glu Thr Gly Ile Asn Thr Gly Ser Gln
            340                 345                 350
Glu Leu Leu Ser Glu Thr Gly Ile Ser Leu Asp Pro Arg Lys Pro Ala
        355                 360                 365
Ser Gln Cys Val Leu Asp Gly Val Arg Gly Cys Asp Ser Tyr Met Val
    370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
                405                 410                 415
Gln Leu Pro Ile Ile Gln Leu Arg Lys Val Trp Ala Glu Ala Val His
            420                 425                 430
Tyr Val Ser Gly Leu Lys Glu Asp Tyr Ser Arg Leu Phe Gln Gly Gln
        435                 440                 445
Arg Ala Ala
    450
```

<210> SEQ ID NO 2
<211> LENGTH: 1406
<212> TYPE: DNA
<213> ORGANISM: Homo Sapiens

<400> SEQUENCE: 2

```
gggaccggcc ttagaccggc ggcgttgcct gaggcggctg gcgctcccgc cccatggagc      60
ggccccccggg gctgcggccg ggcgcgggcg gcccctggga gatgcgggaa cggcttggca    120
ccggcggttt cgggaacgtc agtctgtacc agcaccggga acttgatctc aaaatagcaa    180
ttaagtcttg tcgtttagag ctaagttcca aaaacagaga gcgatggtgc catgaaatcc    240
agatcatgaa aaagttggac catgcgaatg ttgtaaaggc ctgtgatgtc cctgaggaat    300
tgaactttt aattaacgat gtgcctcttc tggcaatgga gtactgttct ggaggggacc    360
tccggaagct actcaacaaa ccagaaaatt gttgtggact aaagaaagc cagatacttt    420
```

-continued

```
ctttactgag tgacatagga tctgggatcc gatatctgca tgaaaacaaa attatacatc     480
gagatctaaa acctgaaaat atagttcttc aagatgttgg tgggaagaca atacataaaa     540
taattgattt gggttatgcc aaagatgttg atcaaggaag tctctgtaca tcttttgtgg     600
gaacattgca gtatttggcc ccagagctct ttgaaaataa gccgtacaca gccactgtgg     660
attattggag ctttgggacc atggtgtttg aatgtattgc tggatatagg ccttttttgc     720
atcatctgca gccatttacc tggcatgaga agattaagaa gaaagatcca aagtgtatat     780
ttgcatgtga agagatgact ggagaagttc ggtttagtag ccatttacct cagccaaaca     840
gcctttgtag tttaatagta gagccaatgg aaagctggct ccaattgatg ctgaattggg     900
acccacagca gagaggggga cctattgatc ttactttgaa gcagccaaga tgttttgcat     960
taatggatca cattctcaat ttaaagatag tgcacatcct aaatatgact tctgcaaaaa    1020
tcatttcttt tctgttacca tgtgatgaaa gtcttcattc actacagtct cgaattgagc    1080
gtgaaacagg aataaataca ggttctcagg agcttctgtc agagacaggg atttctctgg    1140
atcctcggaa accagcctct cagtgtgttc tagatggagt tagaggctgt gatagctaca    1200
tggtttattt gtttgataaa agtaagactg tatatgaagg accatttgca tccagaagtt    1260
tatctgattg tgtaaattat attgtacaag acagcaaaat acaactgcca attatacagc    1320
tgcggaaagt atgggctgaa gcagtgcact acgtatctgg gctaaaggaa gactacagca    1380
ggctcttcca gggacaaaga gcagca                                         1406
```

<210> SEQ ID NO 3
<211> LENGTH: 20
<212> TYPE: PRT
<213> ORGANISM: Mouse

<400> SEQUENCE: 3

Ile Phe Arg Lys Asn Val Lys Ser Met Glu Arg Asn Gly Arg Lys Gly
1               5                   10                  15

His Ser Leu Phe
        20

<210> SEQ ID NO 4
<211> LENGTH: 471
<212> TYPE: PRT
<213> ORGANISM: Mouse

<400> SEQUENCE: 4

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Ser Leu Tyr
            20                  25                  30

Gln His Arg Glu Leu Asp Leu Lys Ile Ala Ile Lys Ser Cys Arg Leu
        35                  40                  45

Glu Leu Ser Ser Lys Asn Arg Glu Arg Trp Cys His Glu Ile Gln Ile
    50                  55                  60

Met Lys Lys Leu Asp His Ala Asn Val Val Lys Ala Cys Asp Val Pro
65                  70                  75                  80

Glu Glu Leu Asn Phe Leu Ile Asn Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

```
Gly Ser Gly Ile Arg Tyr Leu His Glu Asn Lys Ile Ile His Arg Asp
        130                 135                 140
Leu Lys Pro Glu Asn Ile Val Leu Gln Asp Val Gly Lys Thr Ile
145                 150                 155                 160
His Lys Ile Ile Asp Leu Gly Tyr Ala Lys Asp Val Asp Gln Gly Ser
                165                 170                 175
Leu Cys Thr Ser Phe Val Gly Thr Leu Gln Tyr Leu Ala Pro Glu Leu
            180                 185                 190
Phe Glu Asn Lys Pro Tyr Thr Ala Thr Val Asp Tyr Trp Ser Phe Gly
        195                 200                 205
Thr Met Val Phe Glu Cys Ile Ala Gly Tyr Arg Pro Phe Leu His His
    210                 215                 220
Leu Gln Pro Phe Thr Trp His Glu Lys Ile Lys Lys Asp Pro Lys
225                 230                 235                 240
Cys Ile Phe Ala Cys Glu Glu Met Thr Gly Glu Val Arg Phe Ser Ser
                245                 250                 255
His Leu Pro Gln Pro Asn Ser Leu Cys Ser Leu Ile Val Glu Pro Met
            260                 265                 270
Glu Ser Trp Leu Gln Leu Met Leu Asn Trp Asp Pro Gln Gln Arg Gly
        275                 280                 285
Gly Pro Ile Asp Leu Thr Leu Lys Gln Pro Arg Cys Phe Ala Leu Met
    290                 295                 300
Asp His Ile Leu Asn Leu Lys Ile Val His Ile Leu Asn Met Thr Ser
305                 310                 315                 320
Ala Lys Ile Ile Ser Phe Leu Leu Pro Cys Asp Glu Ser Leu His Ser
                325                 330                 335
Leu Gln Ser Arg Ile Glu Arg Glu Thr Gly Ile Asn Thr Gly Ser Gln
            340                 345                 350
Glu Leu Leu Ser Glu Thr Gly Ile Ser Leu Asp Pro Arg Lys Pro Ala
        355                 360                 365
Ser Gln Cys Val Leu Asp Gly Val Arg Gly Cys Asp Ser Tyr Met Val
    370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
                405                 410                 415
Gln Leu Pro Ile Ile Gln Leu Arg Lys Val Trp Ala Glu Ala Val His
            420                 425                 430
Tyr Val Ser Gly Leu Lys Glu Asp Tyr Ser Arg Leu Phe Gln Gly Gln
        435                 440                 445
Arg Ala Ala Ile Phe Arg Lys Asn Val Lys Ser Met Glu Arg Asn Gly
    450                 455                 460
Arg Lys Gly His Ser Leu Phe
465                 470

<210> SEQ ID NO 5
<211> LENGTH: 3314
<212> TYPE: DNA
<213> ORGANISM: Mouse

<400> SEQUENCE: 5
gggaccggcc ttagaccggc ggcgttgcct gaggcggctg gcgctcccgc cccatggagc     60
ggcccccggg gctgcggccg ggcgcgggcg gccccctggga gatgcgggaa cggcttggca    120
```

-continued

```
ccggcggttt cgggaacgtc agtctgtacc agcaccggga acttgatctc aaaatagcaa    180
ttaagtcttg tcgtttagag ctaagttcca aaaacagaga gcgatggtgc catgaaatcc    240
agatcatgaa aaagttggac catgcgaatg ttgtaaaggc ctgtgatgtc cctgaggaat    300 tgaactttt aattaacgat gtgcctcttc tggcaatgga gtactgttct ggaggggacc    360
tccggaagct actcaacaaa ccagaaaatt gttgtggact aaagaaagc cagatacttt     420 ctttactgag tgacatagga tctgggatcc gatatctgca tgaaaacaaa attatacatc    480
gagatctaaa acctgaaaat atagttcttc aagatgttgg tgggaagaca atacataaaa    540
taattgattt gggttatgcc aaagatgttg atcaaggaag tctctgtaca tcttttgtgg    600
gaacattgca gtatttggcc ccagagctct tgaaaataa gccgtacaca gccactgtgg     660
attattggag ctttgggacc atggtgtttg aatgtattgc tggatatagg ccttttttgc    720
atcatctgca gccatttacc tggcatgaga agattaagaa gaaagatcca aagtgtatat    780
ttgcatgtga agagatgact ggagaagttc ggtttagtag ccatttacct cagccaaaca    840
gcctttgtag tttaatagta gagccaatgg aaagctggct ccaattgatg ctgaattggg    900
acccacagca gagagggga cctattgatc ttactttgaa gcagccaaga tgttttgcat     960
taatggatca cattctcaat ttaaagatag tgcacatcct aaatatgact tctgcaaaaa    1020
tcatttcttt tctgttacca tgtgatgaaa gtcttcattc actacagtct cgaattgagc    1080
gtgaaacagg aataaataca ggttctcagg agcttctgtc agagacaggg atttctctgg    1140
atcctcggaa accagcctct cagtgtgttc tagatggagt tagaggctgt gatagctaca    1200
tggtttattt gtttgataaa agtaagactg tatatgaagg accatttgca tccagaagtt    1260
tatctgattg tgtaaattat attgtacaag acagcaaat acaactgcca attatacagc     1320
tgcggaaagt atgggctgaa gcagtgcact acgtatctgg gctaaaggaa gactacagca    1380
ggctcttcca gggacaaaga gcagcaatct tcagaaaaaa tgttaaaagc atggaaagaa    1440
atggaagaaa aggccattca ctattctgag gttggtgtca ttggttatct tgaggatcaa    1500
attatgtctt tgcacactga aatcatggag ctgcagaaga gccctacgg acgacgccag      1560 ggagacttga tggagtctct ggagcagcgt gccattgatc tctataagca gctaaagcac    1620
agacctcctg atcacttgta cagcgacagc acagagatgg tgaagatcat cgtgcacacc    1680
gtgcagagtc aggaccgtgt tctcaaggag ctgtttggtc acctgagcaa gttgttgggc    1740
tgcaagcaga agattattga tctactcccc aaggtggaag tggccctcag taacatcaaa    1800
gaagctgaca atactgtcat gtttatgcag ggaaagaggg agaaagaaat ttggcacctc    1860
cttaaaattg cctgtacaca gagttctgcc cgctctcttg taggatccag tctagaaggc    1920
acagtaaccc ctccagtatc agcatggctg ccccctacat tagcagaccg tgaacatcct    1980
ctgacatgtg tggtaactcc tcaagatgga gagacgttag cacaaatgat agaagaaaat    2040
ctgaactgtc ttggccattt aagtactatt attcgtgaag caaatgagga ccagagcagt    2100
agtttgatga gtcttgattg gagttggtta gcagaatgac tcgacactcg ttcactgtcc    2160
tggagcctac gaagctgttt tgtcatttac tccaaagtca tctttacttg ctgaagccat    2220
tcctcactta ccagtccgtg aggagatggc tgtgatcgga aactacgagt gactttacaa    2280
gcacagtagc ttggtgtttt gtttgtttct aataattatg atctctgaac agatagaatt    2340
ttatagcaaa ttagtgaaat taattattct ttttaacacc gcaactaatg agggagatca    2400
ttagtgacct gctatctta taaaattgga aaaatactac tactagttta gctgatgaaa     2460
aagataatct tctaaaggcc taaattttcg gcataaggcc caacatggta ttagtataca    2520
```

-continued

```
ggaatgaaaa attcacccag tgttcatttg aagtaaagtt ttatctatgg gtttctgtg     2580 gaagagactg ctgacaagta aaattgctct tcctgaagac taagcccagc ctccttgtgt     2640
tgctctcagc aagtgttctt catggcatca catggagtca gatgaatccc atctttaatc     2700
acacatttaa tagagtcctt ttcctgtgta aggggttgga cttttgtgcc tttgatatca     2760
gctgaccata atgaattgtg ttgtgtgcta tatgtatatg tatttaaggt gtacatttaa     2820
taatatcaaa gagaagatgc ctgttaattt ataatgtatt tgaaagttgt attgttttg     2880 catttgtaaa aatgggttac ttgtttaaac aatcttttat gtcttgtcat acaaattcca     2940
aagggtctgc attcctttat ctgtaattac agtctcagaa tccaagttct gaaaacaagg     3000
tatctattct gatctgacac tggatctgct tatcccattt agtgtgaata ttcattgatt     3060
tatgtgtttg attattggga tgtgctgcca caggctctct tgaaggttga tgtagtgtgg     3120
cgtatgcact gaattacctt tctaaaatct gaacagttct cattctgaaa catctagact     3180
taagggtttc agataaaaga ctgcggttct ctgccttatg ttaaataact tagaagatgt     3240
tattttgttt gaaaaaatgt gaaatgcttt tatattctag ttttcacttt tgcatattaa     3300
atgattttaa aatt                                                      3314

<210> SEQ ID NO 6
<211> LENGTH: 1875
<212> TYPE: DNA
<213> ORGANISM: Mouse

<400> SEQUENCE: 6
gggaccggcc ttagaccggc ggcgttgcct gaggcggctg gcgctcccgc cccatggagc       60
ggcccccggg gctgcggccg ggcgcgggcg gccctggga gatgcgggaa cggcttggca      120
ccggcggttt cgggaacgtc agtctgtacc agcaccggga acttcatctc aaaatagcaa      180
ttaagtcttg tcgtttagag ctaagttcca aaaacagaga gcgatggtgc catgaaatcc      240
agatcatgaa aaagttggac catgcgaatg ttgtaaaggc ctgtgatgtc cctgaggaat      300 tgaactttt aattaacgat gtgcctcttc tggcaatgga gtactgttct ggaggggacc      360
tccggaagct actcaacaaa ccagaaaatt gttgtggact aaagaaagc cagatacttt      420 ctttactgag tgcatagga tctgggatcc gatatctgca tgaaaacaaa attatacatc      480
gagatctaaa acctgaaaat atagttcttc aagatgttgg tgggaagaca atacataaaa      540
taattgattt gggttatgcc aaagatgttg atcaaggaag tctctgtaca tctttttgtgg     600 gaacattgca gtatttggcc ccagagctct ttgaaaataa gccgtacaca gccactgtgg      660
attattggag cttgggacc atggtgtttg aatgtattgc tggatatagg ccttttttgc      720
atcatctgca gccatttacc tggcatgaga agattaagaa gaaagatcca agtgtatat       780 ttgcatgtga agatgtgact ggagaagttc ggtttagtag ccatttacct cagccaaaca      840
gcctttgtag tttaatagta gagccaatgg aaagctggct ccaattgatg ctgaattggg      900
acccacagca gagagggga cctattgatc ttactttgaa gcagccaaga tgttttgcat      960
taatggatca cattctcaat ttaaagatag tgcacatcct aaatatgact tctgcaaaaa     1020
tcatttcttt tctgttacca tgtgatgaaa gtcttcattc actacagtct cgaattgagc     1080
gtgaaacagg aataaataca ggttctcagg agcttctgtc agagacaggg atttctctgg     1140
atcctcggaa accagcctct cagtgtgttc tagatggagt taggctgt gatagctaca      1200 tggtttattt gtttgataaa agtaagactg tatatgaagg accatttgca tccagaagtt     1260
```

-continued

| | |
|---|---|
| tatctgattg tgtaaattat attgtaccaa gacagcaaaa tacaactgcc aattatacag | 1320 |
| ctgcggaaag tatgggctga agcagtgcac tacgtatctg ggctaaagga agactacagc | 1380 |
| aggctcttcc agggacaaag agcagcaatc ttcagaaaaa atgttaaaag catggaaaga | 1440 |
| aatggaagaa aaggccattc actattctga ggttggtgtc attggttatc ttgaggatca | 1500 |
| aattatgtct ttgcacactg aaatcatgga gctgcagaag agcccctacg gacgacgcca | 1560 |
| gggagacttg atggagtctc tggagcagcg tgccattgat ctctataagc agctaaagca | 1620 |
| cagacctcct ggtaagacac ttcagtcaca gtattgaaag gtggtttagg aaacacccta | 1680 |
| actgaacaaa gtgggtaaat tttaatgttt tttaacttca tagtatgatc ctgttttggt | 1740 |
| attcttttg caacatttgt ggcataatag ctttaaattt ataaaaactt aaaagattag | 1800 |
| aagaggaaag taataaggat attgaagtag aaaagttta aaagtgaagt gaaaagaaag | 1860 |
| tagagaagaa aaaaa | 1875 |

<210> SEQ ID NO 7
<211> LENGTH: 25
<212> TYPE: DNA
<213> ORGANISM: Homo sapiens

<400> SEQUENCE: 7

| | |
|---|---|
| tagagaaccg cactgcttac tggct | 25 |

<210> SEQ ID NO 8
<211> LENGTH: 20
<212> TYPE: DNA
<213> ORGANISM: Homo sapiens

<400> SEQUENCE: 8

| | |
|---|---|
| ggcggctcgc tgtccctgct | 20 |

<210> SEQ ID NO 9
<211> LENGTH: 19
<212> TYPE: DNA
<213> ORGANISM: Homo sapiens

<400> SEQUENCE: 9

| | |
|---|---|
| cgatggacta caaagacga | 19 |

<210> SEQ ID NO 10
<211> LENGTH: 22
<212> TYPE: DNA
<213> ORGANISM: Homo sapiens

<400> SEQUENCE: 10

| | |
|---|---|
| caagtttcac gctcaatacg ag | 22 |

<210> SEQ ID NO 11
<211> LENGTH: 20
<212> TYPE: DNA
<213> ORGANISM: Homo sapiens

<400> SEQUENCE: 11

| | |
|---|---|
| acactgtcct gttggatgaa | 20 |

<210> SEQ ID NO 12
<211> LENGTH: 19
<212> TYPE: DNA
<213> ORGANISM: Mouse

<400> SEQUENCE: 12

```
ctctatgcat ccatgacat                                            19

<210> SEQ ID NO 13
<211> LENGTH: 21
<212> TYPE: DNA
<213> ORGANISM: Mouse

<400> SEQUENCE: 13
ccaactctta gactacgaca g                                         21

<210> SEQ ID NO 14
<211> LENGTH: 20
<212> TYPE: DNA
<213> ORGANISM: Mouse

<400> SEQUENCE: 14
ctctatgacc tccatgacat                                           20

<210> SEQ ID NO 15
<211> LENGTH: 29
<212> TYPE: DNA
<213> ORGANISM: Homo sapiens
<220> FEATURE:
<221> NAME/KEY: misc_feature
<222> LOCATION: (28)..(28)
<223> OTHER INFORMATION: v=3' terminal position is degenerate, refers to
      a, g, or c.
<220> FEATURE:
<221> NAME/KEY: misc_feature
<222> LOCATION: (29)..(29)
<223> OTHER INFORMATION: n=refers to all four DNA nucleotides.

<400> SEQUENCE: 15
agctccggaa ttcggttttt tttttttvn                                 29

<210> SEQ ID NO 16
<211> LENGTH: 24
<212> TYPE: DNA
<213> ORGANISM: Mouse

<400> SEQUENCE: 16
accatttgca tccagaagtt tatc                                      24

<210> SEQ ID NO 17
<211> LENGTH: 22
<212> TYPE: DNA
<213> ORGANISM: Mouse

<400> SEQUENCE: 17
caggaggtct gtgctttagc tg                                        22

<210> SEQ ID NO 18
<211> LENGTH: 21
<212> TYPE: DNA
<213> ORGANISM: Mouse

<400> SEQUENCE: 18
tgctcaggtg accaaacagc t                                         21

<210> SEQ ID NO 19
<211> LENGTH: 24
<212> TYPE: DNA
<213> ORGANISM: Mouse

<400> SEQUENCE: 19
```

```
gcaaaaagaa taccaaaaca ggat                                          24

<210> SEQ ID NO 20
<211> LENGTH: 22
<212> TYPE: DNA
<213> ORGANISM: Mouse

<400> SEQUENCE: 20
gataaccaat gacaccaacc tc                                            22
```